US012776028B2

(12) United States Patent
Bao et al.

(10) Patent No.: US 12,776,028 B2
(45) Date of Patent: Oct. 27, 2026

(54) METHODS AND SYSTEMS FOR IMAGE ACQUISITION, IMAGE QUALITY EVALUATION, AND MEDICAL; IMAGE ACQUISITION

(71) Applicant: SHANGHAI UNITED IMAGING HEALTHCARE CO., LTD., Shanghai (CN)

(72) Inventors: Yuan Bao, Shanghai (CN); Wei Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 637 days.

(21) Appl. No.: 18/049,277

(22) Filed: Oct. 24, 2022

(65) Prior Publication Data

US 2023/0063828 A1 Mar. 2, 2023

Related U.S. Application Data

(63) Continuation of application No. PCT/CN2021/089454, filed on Apr. 23, 2021.

(30) Foreign Application Priority Data

Apr. 23, 2020 (CN) ......................... 202010327417.4
May 6, 2020 (CN) ......................... 202010374378.3

(51) Int. Cl.
*G06T 7/00* (2017.01)
*A61B 6/00* (2006.01)
(Continued)

(52) U.S. Cl.
CPC ............ *G06T 7/0012* (2013.01); *A61B 6/545* (2013.01); *G06T 7/70* (2017.01); *G06V 10/44* (2022.01);
(Continued)

(58) Field of Classification Search
CPC ....... G06T 7/0002; G06T 7/0012–0016; G06T 2207/10064–10136;
(Continued)

(56) References Cited

U.S. PATENT DOCUMENTS 8,957,955 B2 * 2/2015 Reiner ................... G16H 40/40 702/81
10,467,507 B1 * 11/2019 Hao .................... G06F 18/2415
(Continued)

FOREIGN PATENT DOCUMENTS

CN 104068886 A 10/2014
CN 107582085 A 1/2018
(Continued)

OTHER PUBLICATIONS

Belli, D., & Kipf, T. (2019). Image-conditioned graph generation for road network extraction. arXiv preprint arXiv:1910.14388. (Year: 2019).*

(Continued)

*Primary Examiner* — Andrew W Bee
*Assistant Examiner* — Emma E Dryden
(74) *Attorney, Agent, or Firm* — METIS IP LLC

(57) ABSTRACT

The embodiment of the present disclosure discloses a method and a system for image acquisition, image quality evaluation, and medical image acquisition. The image acquisition method comprises obtaining an image of a target subject; obtaining, based on one or more evaluation models, one or more scores related to one or more evaluation indexes of the image; obtaining a quality evaluation result of the image based on the one or more scores related to the one or more evaluation indexes; and determining one or more acquisition parameters based on the quality evaluation result.

17 Claims, 9 Drawing Sheets

200

(51) Int. Cl.

| | |
|---|---|
| ***G06T 7/70*** | (2017.01) |
| ***G06V 10/44*** | (2022.01) |
| ***G06V 10/764*** | (2022.01) |
| ***G06V 10/98*** | (2022.01) |
| ***G16H 40/60*** | (2018.01) |

(52) U.S. Cl.

CPC ............ *G06V 10/764* (2022.01); *G06V 10/98* (2022.01); *G06V 10/993* (2022.01); *G16H 40/60* (2018.01); *G06T 2207/10072* (2013.01); *G06T 2207/10081* (2013.01); *G06T 2207/10116* (2013.01); *G06T 2207/30168* (2013.01); *G06V 2201/03* (2022.01)

(58) Field of Classification Search

CPC ..................... G06T 2207/30004–30104; G06T 2207/30168; G06T 9/20; G06T 11/203; G06T 7/12; G06T 7/149; G06T 17/00; G06T 2207/10028; G06T 7/73; G06T 7/74; G06V 2201/03–034; G06V 10/993; G06V 10/44–46; G06V 10/764; G06V 10/77; G06V 10/98; G06V 10/478; G06V 30/18; G06V 20/64; A61B 6/032; A61B 6/037; A61B 5/055; A61B 6/52; A61B 6/5217; A61B 5/0037; A61B 6/5211; A61B 6/5205; A61B 5/0263; A61B 6/48; A61B 6/54; A61B 6/545–548; A61B 6/5258; A61B 5/7203; A61B 6/5294; G16H 30/40; G16H 50/20; G16H 40/60; G16H 30/20

See application file for complete search history.

(56) References Cited

U.S. PATENT DOCUMENTS

| | | | | |
|---|---|---|---|---|
| 2005/0251013 | A1* | 11/2005 | Krishnan | G06T 7/0012 600/407 |
| 2009/0116710 | A1 | 5/2009 | Futami et al. | |
| 2011/0110572 | A1* | 5/2011 | Guehring | A61B 6/5258 382/128 |
| 2014/0037194 | A1* | 2/2014 | Kitamura | G06T 7/344 382/154 |
| 2014/0275945 | A1 | 9/2014 | Fonte et al. | |
| 2015/0104092 | A1* | 4/2015 | Flohr | A61B 6/08 382/131 |
| 2015/0230769 | A1 | 8/2015 | Tsuyuki | |
| 2016/0042012 | A1 | 2/2016 | Lou et al. | |
| 2017/0316562 | A1 | 11/2017 | Haberland et al. | |
| 2018/0140270 | A1* | 5/2018 | Profio | A61B 5/055 |
| 2019/0150857 | A1* | 5/2019 | Nye | G16H 30/40 |
| 2020/0160124 | A1* | 5/2020 | Fu | G06V 10/764 |
| 2020/0176107 | A1* | 6/2020 | Sevenster | G16H 30/20 |
| 2020/0187887 | A1* | 6/2020 | Alon Cohen | A61B 6/547 |
| 2020/0402229 | A1* | 12/2020 | Chen | G06T 7/11 |
| 2021/0093301 | A1* | 4/2021 | Wang | A61B 8/463 |
| 2022/0130520 | A1* | 4/2022 | Xia | G16H 50/30 |
| 2022/0139529 | A1* | 5/2022 | Bhatia | G16H 30/20 382/131 |
| 2022/0165395 | A1* | 5/2022 | Patil | G06F 11/3058 |
| 2022/0338819 | A1* | 10/2022 | Stayman | G16H 30/40 |
| 2023/0071400 | A1* | 3/2023 | Abdolell | G06T 7/0012 |

FOREIGN PATENT DOCUMENTS

| | | | | | |
|---|---|---|---|---|---|
| CN | 107802265 | A | | 3/2018 | |
| CN | 108257132 | A | | 7/2018 | |
| CN | 108986075 | A | * | 12/2018 | G06T 7/0002 |
| CN | 109276269 | | | 1/2019 | |
| CN | 109276269 | A | * | 1/2019 | |
| CN | 109350100 | A | | 2/2019 | |
| CN | 109949264 | A | | 6/2019 | |
| CN | 110507337 | A | | 11/2019 | |
| CN | 110772210 | A | | 2/2020 | |
| CN | 111028218 | A | | 4/2020 | |
| CN | 111462112 | | | 7/2020 | |
| CN | 111528879 | | | 8/2020 | |
| JP | 2004321587 | A | | 11/2004 | |
| JP | 2012130542 | A | | 7/2012 | |
| KR | 20200005413 | A | * | 1/2020 | G16H 50/20 |

OTHER PUBLICATIONS

Booij, R., van Straten, M., Wimmer, A., & Budde, R. P. (2018). Automated patient positioning in CT using a 3D camera for body contour detection: accuracy in pediatric patients. European radiology, 31(1), 131-138. (Year: 2018).*

Liu, T. J., Lin, W., & Kuo, C. C. J. (2013). Image quality assessment using multi-method fusion. IEEE Transactions on image processing, 22(5), 1793-1807. (Year: 2013).*

Liu, Zhe et al., Clothing CAD application (I), China Light Industry Press, 2011, 4 pages.

The Partial European Search Report in European Application No. 21791868.9 mailed on Sep. 20, 2023, 18 pages.

International Search Report in PCT/CN2021/089454 mailed on Jul. 21, 2021, 7 pages.

Written Opinion in PCT/CN2021/089454 mailed on Jul. 21, 2021, 12 pages.

Feng, Youzhen et al., Essentials of Modern Clinical Imaging Diagnosis (I), Jilin Science and Technology Press, 2019, 10 pages.

First Office Action in Chinese Application No. 202510191158.X mailed on Nov. 5, 2025, 15 pages.

Communication Pursuant to Article 94(3) EPC in European Application No. 21791868.9 mailed on May 11, 2026, 11 pages.

Tang, Guangjian et al., Modern Whole Body CT Diagnostics 3rd Edition, China Medical Science and Technology Press, 2013, 20 pages.

* cited by examiner

200

METHODS AND SYSTEMS FOR IMAGE ACQUISITION, IMAGE QUALITY EVALUATION, AND MEDICAL; IMAGE ACQUISITION

CROSS REFERENCE

The present application is a continuation of International Application No. PCT/CN2021/089454, filed on Apr. 23, 2021, which claims priority of Chinese application No. 202010327417.4, filed on Apr. 23, 2020, and Chinese application No. 202010374378.3, filed on May 6, 2020, the entire contents of each of which are incorporated herein by reference.

TECHNICAL FIELD

The present disclosure relates to the field of image processing, in particular to a method and system for image acquisition, image quality evaluation, and medical image acquisition.

BACKGROUND

Radiological devices (such as DR devices, CT devices, breast X-ray machines, etc.) may conduct image acquisition and/or treatment for patients by emitting radiation (such as X-rays). In the existing technology, the acquisition parameters used by the radiation device are generally the default acquisition parameters of the radiation device. After the image is acquired, it is necessary to evaluate whether the quality of the acquired image meets the diagnostic requirements. If the quality of the acquired image does not meet the diagnostic requirements, the technician will manually adjust the acquisition parameters according to experience. However, medical image processing includes a heavy workload. When doctors evaluate image quality, they need to make comprehensive evaluations from multiple dimensions. The workload is heavy, and it is required that the evaluation personnel is experienced, which is very prone to miscalculation. Most of the existing evaluation methods allow doctors to evaluate the image quality by experience, and the efficiency and quality of evaluation are difficult to be guaranteed. How to determine the image quality and obtain the image that meets the diagnostic requirements is very important.

Therefore, it is necessary to propose a method and system for image acquisition, image quality evaluation, and medical image acquisition to improve the efficiency and quality of image quality evaluation.

SUMMARY

One aspect of the embodiments of the present disclosure provides an image acquisition method. This method includes: obtaining the image of the target subject. Based on one or more evaluation models, one or more scores related to the image and the one or more evaluation indexes are obtained. The one or more evaluation indexes include one or more of an anatomical structure clarity, a target portion contrast, an image signal uniformity, an image noise level, an artifact suppression degree, a window width, a window level, whether the image has foreign objects, and a location accuracy of imaged portion; the one or more scores related to the one or more evaluation indexes are obtained based on different evaluation models respectively; obtaining the quality evaluation result of the image based on the one or more scores related to the one or more evaluation indexes; determining the one or more acquisition parameters based on the quality evaluation result.

Another aspect of the embodiments of the present disclosure provides an image acquisition system. The system includes: an image obtaining module, configured to obtain an image of a target subject; an evaluation index determining module, configured to obtain one or more scores related to one or more evaluation indexes of the image based on one or more evaluation models, wherein the one or more evaluation indexes include one or more of: an anatomical structure clarity, a target portion contrast, an image signal uniformity, an image noise level, an artifact suppression degree, a window width, a window level, whether the image includes a foreign object, and a location accuracy of an imaged portion, and the one or more scores related to the one or more evaluation indexes are obtained based on different evaluation models, respectively; a quality evaluation result obtaining module, configured to acquire a quality evaluation result of the image based on the one or more scores related to the one or more evaluation indexes; and an acquisition parameter determination module, configured to determine one or more acquisition parameters based on the quality evaluation result.

Another aspect of the embodiments of the present disclosure provides a method for evaluating image quality. The method for evaluating the image quality includes: acquiring an image to be evaluated. The one or more scores of the image to be evaluated related to the one or more evaluation indexes may be obtained based on one or more evaluation models, and the one or more evaluation indexes include one or more of anatomical structure clarity, target portion contrast, image signal uniformity, image noise level, and artifact suppression degree. The one or more scores related to the one or more evaluation indexes are obtained based on different evaluation models, respectively. The quality evaluation result of the image to be evaluated may be obtained based on the one or more scores related to the one or more evaluation indexes.

Another aspect of the present disclosure embodiment provides a system that evaluates image quality. The system includes an obtaining module, which may be used to acquire an image to be evaluated. The first processing module may be used to obtain the one or more scores related to the image to be evaluated based on one or more evaluation models, and the one or more evaluation indexes include one or more of anatomical structure clarity, target portion contrast, image signal uniformity, image noise level, and artifact suppression degree. The one or more scores related to the one or more evaluation indexes are obtained based on different evaluation models. The second processing module may be used to obtain the quality evaluation result of the image to be evaluated based on the one or more scores related to the one or more evaluation indexes.

Another aspect of the embodiment of the present disclosure provides a device that evaluates the quality of the image includes at least one storage medium and at least one processor, which is used at least one storage medium for storage computer instructions. The at least one processor is used to execute the computer instruction to realize a method for evaluating image quality.

Another aspect of the embodiments of the present disclosure provides a computer-readable storage medium, which stores computer instructions. When the computer reads the computer instructions in the storage medium, the computer executes a method for evaluating image quality.

Another aspect of the embodiments of the present disclosure provides a method for medical image acquisition, which includes: acquiring the posture information of a subject. Determine whether there is a matching imaging protocol in the historical imaging protocol based on the posture information of the subject at least: if yes, take at least part of the acquisition parameters in the matching imaging protocol as the current acquisition parameters. If it does not exist, apply or at least partially modify the default acquisition parameters or input the acquisition parameters as the current acquisition parameters. Taking the image of the subject based on the current acquisition parameters.

Another aspect of the embodiments of the present disclosure provides a medical image acquisition system, including an obtaining module, a determining module, and a photographing module, wherein: the obtaining module is used to acquire the posture information of the subject to be imaged. The determining module is used to determine whether there is a matching imaging protocol in the historical imaging agreement based on the posture information of the subject: if it exists, the at least part of the collection parameters in the matching imaging protocol are used as the current collection as the current collection parameter. If it does not exist, apply or at least partially modify the default acquisition parameters or input the acquisition parameters as the current acquisition parameters. The photographing module is used for photographing the image of the subject based on the current acquisition parameters.

Another aspect of the embodiments of the present disclosure provides a device for medical image acquisition. The device includes at least one processor and at least one storage device. The storage device is used to store instructions. When the at least one processor executes the instructions, the image acquisition method described in any embodiment of the present disclosure is implemented.

Another aspect of the embodiments of the present disclosure provides a computer-readable storage medium, which stores computer instructions. When the computer reads the computer instructions in the storage medium, the computer executes an image acquisition method as described in any embodiment of the present disclosure.

The methods provided by some embodiments of the present disclosure may effectively reduce the cost of manually evaluating image quality. The may learn a lot of experience in image quality evaluation during training, which may improve the efficiency and accuracy of image quality evaluation. Image quality evaluation may be more objective and accurate. At the same time, according to the result of image quality evaluation, the acquisition parameters of the acquired image may be adjusted to obtain an image with better quality.

The method provided by some embodiments of the present disclosure may obtain the posture information of the subject to be imaged, then automatically match the current acquisition parameters from the historical imaging protocol for imaging and automatically evaluate the quality of the captured image, which may automatically control the image acquisition quality. It may avoid the problem of low imaging efficiency caused by using the default acquisition parameters of the system and the operator manually adjusting the acquisition parameters, and ensure the quality of the captured image.

BRIEF DESCRIPTION OF THE DRAWINGS

The present disclosure will further explain in the form of exemplary embodiments, which will be described in detail by the attached drawings. These embodiments are not restrictive. In these embodiments, the same number represents the same structure, where.

DETAILED DESCRIPTION

Figure 1:
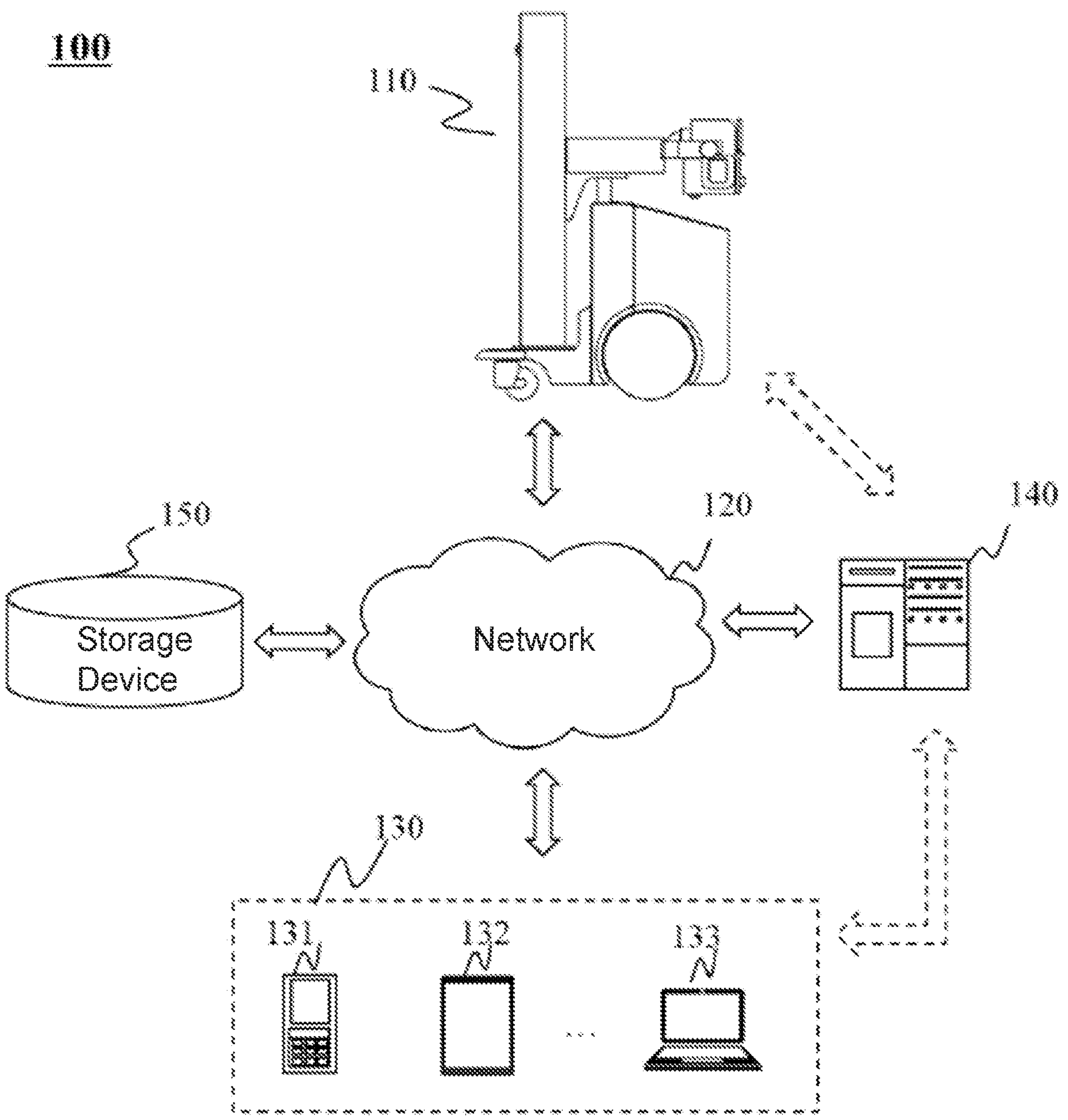
FIG. 1 is a schematic diagram of the medical image system shown in some embodiments of the present disclosure.

In order to more clearly explain the technical solution of the embodiment of the present disclosure, the following will be briefly introduced to the attachment required in the embodiment description. Obviously, the drawings in the following description are just some examples or embodiments of the present disclosure. For ordinary technicians in the art, the present disclosure may also be applied to other similar scenarios according to these drawings without any creative effort. Unless obviously obtained from the context or the context illustrates otherwise, the same numeral in the drawings refers to the same structure or operation.

It should be understood that the "system", "device", "unit" and/or "module" used herein is a method for distinguishing different components, elements, components, parts, or assemblies at different levels. However, if other words may achieve the same purpose, they may be replaced by other expressions.

As shown in the Description and Claims, unless the context clearly indicates an exception, the words "one", "one", "one" and/or "the" do not specifically refer to the singular, but may also include the plural. Generally speaking, the terms "including" and "including" only indicate that steps and elements that have been clearly identified are included, but these steps and elements do not constitute an exclusive list, and methods or devices may also include other steps or elements.

A flowchart is used in the present disclosure to explain the operation performed by the system according to the embodiment of the present disclosure. It should be understood that the previous or back operations may not be accurately implemented in order. Instead, the steps may be processed in reverse order or simultaneously. At the same time, you may add other operations to these procedures, or remove one or more operations from these procedures.

FIG. 1 is a schematic diagram of the application scenario of the medical image system shown in some embodiments of the present disclosure.

The medical image system 100 may include an imaging device 110, a network 120, at least one terminal 130, a processing device 140, and a storage device 150. Various components in the system 100 may be connected to each other through the network 120. For example, the imaging device 110 and at least one terminal 130 may be connected or communicated via the network 120.

The imaging device 110 may include digital radiography (DR), computed radiography (CR), digital fluorescence radiography (DF), magnetic resonance scanner, mammography, CT (computed tomography) imaging device PET (Positron Emission Computed Tomography) imaging device, MRI (Magnetic Resonance Imaging) imaging device, SPECT (Single Photon Emission Computed Tomography) imaging device, PET CT imaging device, PET MRI imaging device, etc.), etc. In some embodiments, the imaging device 110 may include a frame, a detector, a detection area, a scanning table, and a ray generation device (such as a radio source). The rack may be used to support the detector and the ray generator. The scanning table is used to place the subject (also referred to as the target subject in the present disclosure) for scanning. The subject may include a patient, a phantom, or other objects to be scanned. The X-ray generating device may emit X-rays to the subject. The detector may be used to receive X-rays. By scanning the subject, the imaging device 110 may acquire scanning data to generate (or reconstruct) an image.

The network 120 may include any appropriate network that may promote the information and/or data exchange of the medical image system 100. In some embodiments, at least one component of the medical image system 100 (for example, the imaging device 110, the processing device 140, the storage device 150, and at least one terminal 130) may exchange information and/or data with at least one other component of the medical image system 100 through the network 120. For example, the processing device 140 may obtain an image of a subject from the imaging device 110 through the network 120. Network 120 may or may include a public network (for example, the Internet), a private network (for example, a local area network (LAN)), a wired network, a wireless network (for example, an 802.11 network, a Wi-Fi network), a frame relay network, a virtual private network (VPN), a satellite network, a telephone network, a router, a hub, a switch, a server computer, and/or any combination thereof. For example, the network 120 may include a wired network, a wired network, an optical fiber network, a telecommunications network, an intranet, a wireless local area network (WLAN), a metropolitan area network (MAN), a public telephone switching network (PSTN), a Bluetooth™ network, a ZigBee™ network, a near-field communication (NFC) network, or any combination thereof. In some embodiments, network 120 may include at least one network access point. For example, the network 120 may include a wired and/or wireless network access point, such as a base station and/or an Internet switching point, through which at least one component of the medical imaging system 100 may be connected to the network 120 to exchange data and/or information.

At least one terminal 130 may communicate and/or connect with the imaging device 110, the processing device 140, and/or the storage device 150. For example, the operator may adjust the current acquisition parameters of the imaging device 110 through at least one terminal 130. For another example, the operator may enter the imaging protocol through at least one terminal 130 and store the imaging protocol in the storage device 150 by the processing device 140. For another example, the acquisition parameters determined by the processing device 140 may be displayed on the terminal 130. For another example, the image quality evaluation result determined by the processing device 140 may be displayed on the terminal 130. In some embodiments, at least one terminal 130 may include a mobile device 131, a tablet computer 132, a laptop computer 133, or any combination thereof. For example, the mobile device 131 may include a mobile control handle, a personal digital assistant (PDA), a smart phone, or any combination thereof.

In some embodiments, at least one terminal 130 may include an input device, an output device, and the like. The input device may select keyboard input, touch screen (for example, with tactile or tactile feedback) input, voice input, eye tracking input, gesture tracking input, brain monitoring system input, image input, video input, or any other similar input mechanism. The input information received by the input device may be transmitted to the processing device 140 by the bus for further processing. Other types of input devices may include cursor control devices, such as a mouse, a trackball, or cursor direction keys. In some embodiments, an operator (e.g., a technician or a doctor) may input an imaging protocol through an input device. The output device may include a display, a speaker, a printer, or any combination thereof. The output device may be used to output the collection parameters determined by the processing device 140. In some embodiments, at least one terminal 130 may be part of the processing device 140.

The processing device 140 may process data and/or information obtained from the imaging device 110, the storage device 150, at least one terminal 130, or other components of the medical image system 100. For example, the processing device 140 may acquire the posture information of the subject from the imaging device 110. For another example, the processing device 140 retrieves the matching imaging protocol from the historical imaging protocol based on the posture information of the subject, and determines the current acquisition parameters based on this. As another example, the processing device 140 may obtain one or more evaluation models for evaluating image quality based on sample image training. Further, the processing device 140 may use the trained one or more evaluation models to determine the image quality of the medical image acquired by the imaging device 110. In some embodiments, the processing device 140 may be a single server or a group of servers. Server groups may be centralized or distributed. In some embodiments, the processing device 140 may be local or remote. For example, the processing device 140 may access information and/or data from the imaging device 110, the storage device 150, and/or at least one terminal 130 through the network 120. As another example, the processing device 140 may be directly connected to the imaging device 110, at least one terminal 130, and/or the storage device 150 to access information and/or data. In some embodiments, the processing device 140 may be implemented on a cloud platform. For example, cloud platforms may include private cloud, public cloud, hybrid cloud, community cloud, distributed cloud, inter-cloud cloud, multi-cloud, etc., or any combination thereof.

The storage device 150 may store data, instructions, and/or any other information. For example, a historical imaging protocol, an image of a subject, and the like. In some embodiments, the storage device 150 may store data obtained from the imaging device 110, at least one terminal 130, and/or the processing device 140. In some embodiments, the storage device 150 may store data and/or instructions used by the processing device 140 to execute or use to complete the exemplary methods described in the present disclosure. In some embodiments, the storage device 150 may include a mass memory, a removable memory, a volatile read-write memory, a read-only memory (ROM), or any combination thereof. In some embodiments, the storage device 150 may be implemented on a cloud platform.

In some embodiments, the storage device 150 may be connected to the network 120 to communicate with at least one other component in the medical image system 100 (for example, the processing device 140, at least one terminal 130). At least one component of the medical image system 100 may access data (such as historical imaging data) stored in the storage device 150 through the network 120. In some embodiments, the storage device 150 may be part of the processing device 140.

Figure 2:
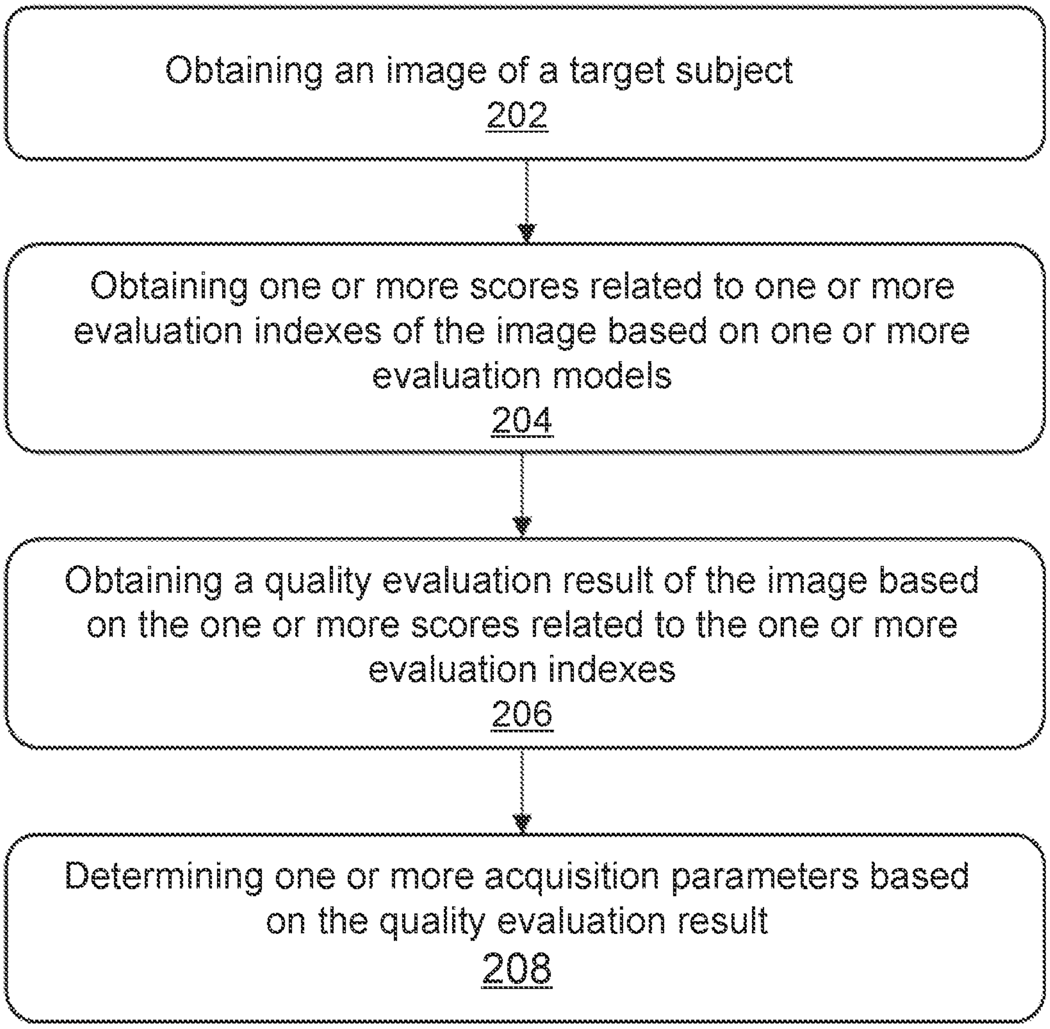
FIG. 2 is a flowchart of an image acquisition method according to some embodiments of the present disclosure.

FIG. 2 is a flowchart of an image acquisition method according to some embodiments of the present disclosure. In some embodiments, the process 200 may be executed by a processing device (e. g., the processing device 140). For example, the process 200 may be stored in a storage device (such as a built-in storage unit or an external storage device of a processing device) in the form of a program or instructions, and the process 200 may be realized when the program or instruction is executed. The process 200 may include the following operations.

In operation 202, an image of the target subject may be obtained. In some embodiments, operation 202 may be performed by the image obtaining module 310.

The target subjects may include patients or other medical experimental objects (for example, experimental mice and other animals). The target subject may also be a part of a patient or other medical experiment object, including organs and/or tissues, such as the heart, lungs, ribs, the abdominal cavity, etc.

In some embodiments, the image of the target subject may be a medical image obtained by processing the scanning projection data obtained by a detection device (such as the detector of the imaging device 110 shown in FIG. 1). In some embodiments, the processing device may directly obtain the image to be evaluated from the scanning device scanning the target subject, such as the scanning device 110, or from the storage device or the medical database.

Figure 7:
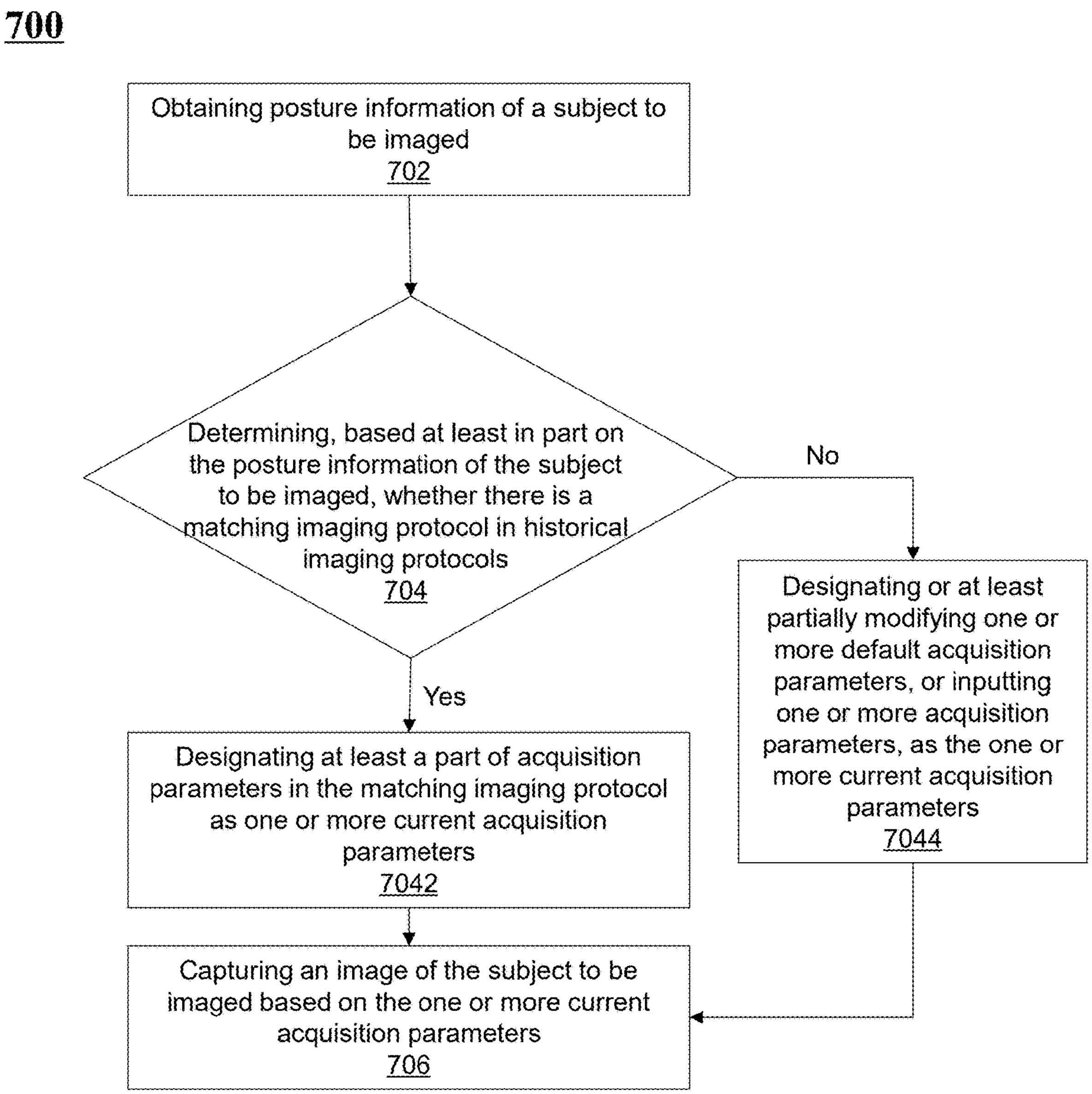
FIG. 7 is a flowchart of a method of medical image acquisition according to some embodiments of the present disclosure.
Figure 8:
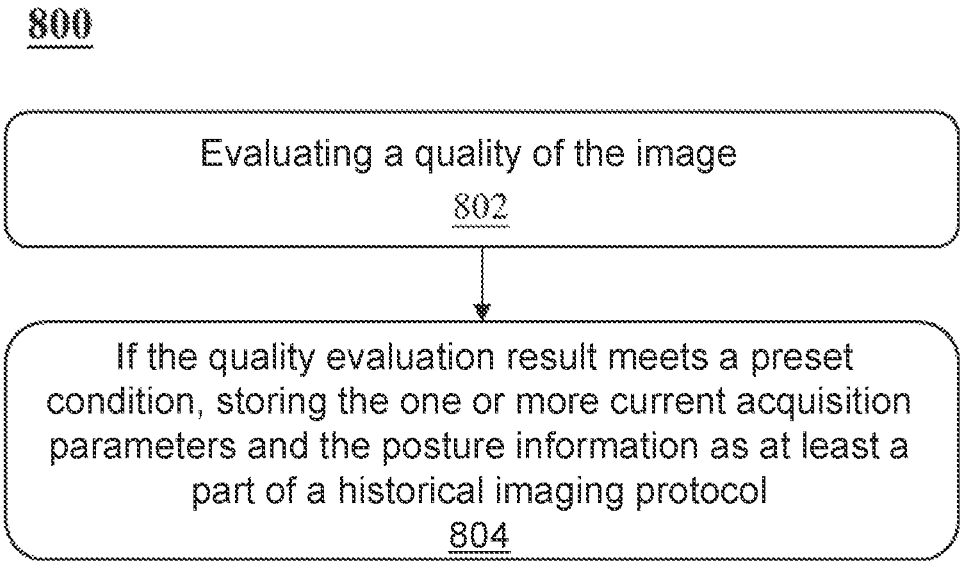
FIG. 8 is a flowchart of a medical image quality evaluation method according to some embodiments of the present disclosure.

In some embodiments, the processing device may also obtain the image of the target subject (the subject to be imaged) through the medical image acquisition method described in some embodiments of the present disclosure, such as FIGS. 7 and 8.

Figure 4:
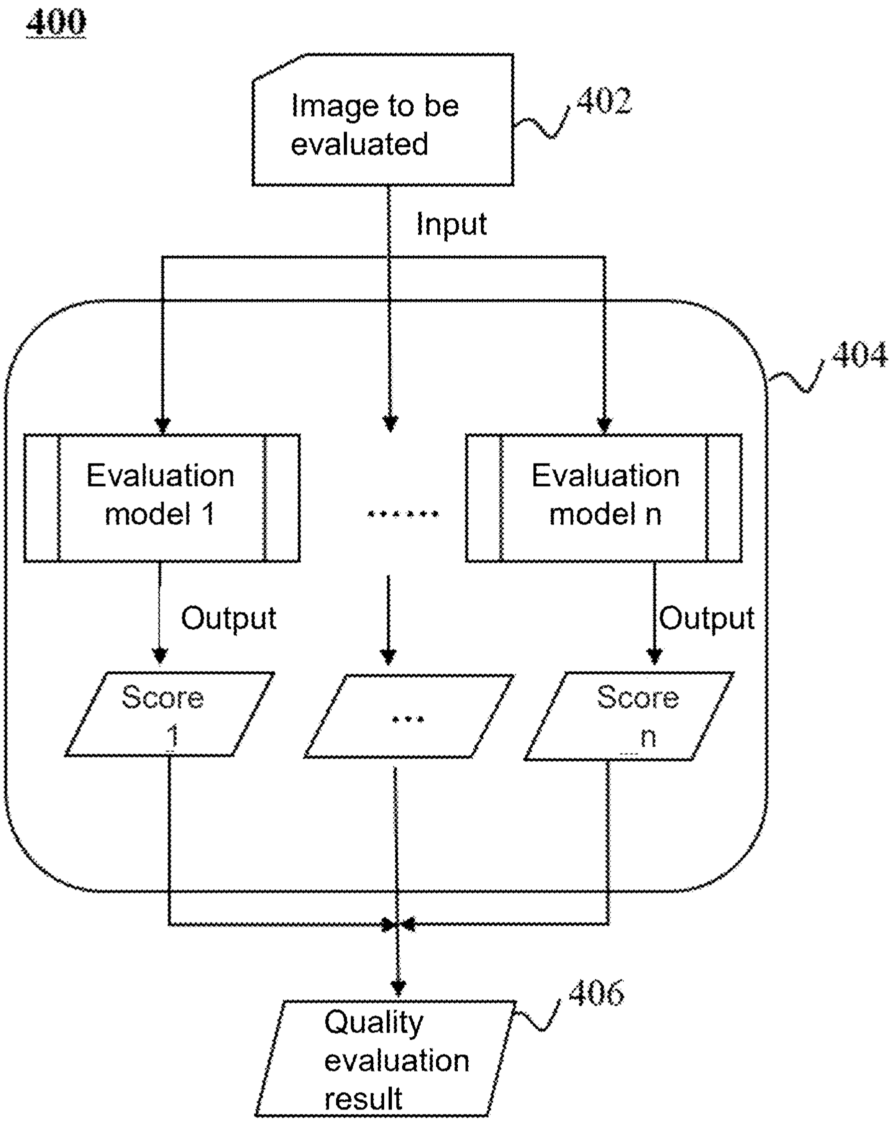
FIG. 4 is a flowchart of a method for determining image quality according to some embodiments of the present disclosure.

For more details on acquiring the image of the target subject, please refer to the description of other relevant parts of the present disclosure, for example, the description of FIGS. 4, 7, and 8, which will not be repeated here.

In operation 204, one or more scores related to one or more evaluation indexes of the image may be obtained based on one or more evaluation models. In some embodiments, operation 204 may be performed by the evaluation index determining module 320.

The evaluation index is a parameter used to measure the quality of the image to be evaluated. In some embodiments, the one or more evaluation indexes may include one or more of anatomical structure clarity, target portion contrast, image signal uniformity, image noise level, artifact suppression degree, window width, window position, whether the image has foreign objects, and the position accuracy of the imaged position. Among them, the position accuracy of the imaged portion may include whether the imaged portion is located in the imaging area, whether the subject to be imaged in the image is located in a better viewing position (for example, whether it is located in the middle of the image, etc.), and so on. For detailed description of other evaluation indexes, please refer to other parts of the present disclosure, for example, FIG. 4-FIG. 5 and related descriptions, which will not be repeated here.

The evaluation model may be trained based on the medical image and/or natural image of the biological tissue and/or organ of the target subject and its corresponding label.

In some embodiments, the one or more scores related to the one or more evaluation indexes are obtained based on different evaluation models. For example, the clarity of anatomical structure is obtained through the evaluation model used to evaluate the clarity of anatomical structure, and the contrast of the target portion is obtained through the evaluation model used to evaluate the contrast of the target portion. The acquisition method may be to input the images into one or more evaluation models respectively, and the one or more scores under different evaluation indexes may be given by one or more evaluation models, for example, the anatomical structure clarity score is 5 points, the contrast of the target portion is 4 points, etc.

For more descriptions of the evaluation model and obtaining one or more scores related to the one or more evaluation indexes, please refer to FIG. 4 and its related descriptions, which will not be repeated here.

In this embodiment, different evaluation models are used to obtain one or more scores related to different evaluation indexes, and the one or more scores are determined based on the one or more evaluation indexes of the image from multiple dimensions, so that accurate evaluations may be made on different types of evaluation indexes. For example, compared with using an evaluation model to score image quality from the perspective of multiple categories of evaluation indexes, using an evaluation model to score one category of evaluation index may make the model pay more attention to the features of the category itself in the evaluation process, thus making more accurate evaluations and improving the accuracy of image quality evaluations.

In some embodiments, multiple evaluation models may also be trained for the same category of evaluation index to further improve the evaluation accuracy of image quality. For example, for the degree of artifact suppression of an image, artifacts may be divided into multiple types, such as bar artifacts, ring artifacts, motion artifacts, etc. Then an evaluation model may be trained for each type of artifact, so that the model may focus more on the evaluation of the type of evaluation index, and further improve the accuracy of evaluation on image quality.

In operation 206, a quality evaluation result of the image may be obtained based on the one or more scores related to the one or more evaluation indexes. In some embodiments, operation 206 may be performed by the quality evaluation result obtaining module 330.

The quality evaluation result may include the overall quality score of the image to be evaluated, and one or more of the image location classification, the image disease classification, and the image artifact classification.

In some embodiments, the processing device may perform a weighted average operation on the one or more scores related to the one or more evaluation indexes to obtain the overall quality score of the image to be evaluated.

Figure 5:
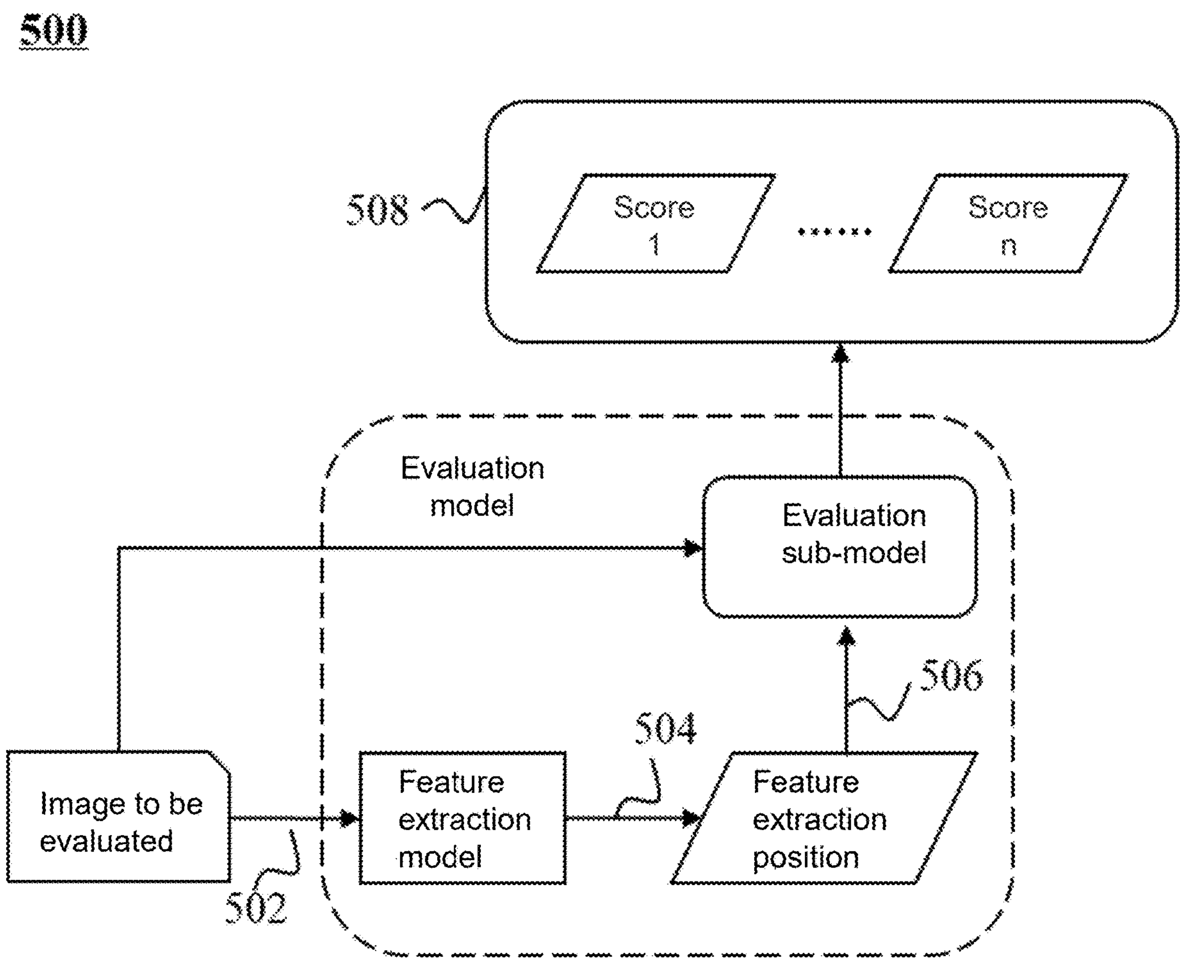
FIG. 5 is a flowchart for obtaining one or more scores related to one or more evaluation indexes according to some embodiments of the present disclosure.

For more description of the quality evaluation result of the acquired image, please refer to the relevant description in FIG. 4 and FIG. 5 of the present disclosure, which will not be repeated here.

In operation 208, one or more acquisition parameters may be determined based on the quality evaluation result. In some embodiments, operation 208 may be performed by the acquisition parameter determination module 340.

Acquisition parameters refer to the parameter information related to image imaging when the imaging device scans or shoots the target subject. For example, acquisition parameters may include the imaging position of the target subject (for example, head, chest, whether the imaging position is located in the scanning or imaging center, etc.), algorithm parameters of image processing (for example, the type of image reconstruction algorithm, for example, iterative reconstruction algorithm, depth learning method, multi-plane reconstruction, etc.), positioning parameters (for example, adjusting the body position of the target subject, etc.) One or more of the ray source parameters (e.g., scanning dose, scanning angle, etc.), filter kernel parameters (e.g., convolution kernel parameters of the filter), image denoising parameters, reconstruction parameters (e.g., size of the reconstruction matrix), artifact suppression parameters (e.g., artifact suppression method), injection parameters (e.g., whether to use contrast agent or tracer, a dose of injection, injection time, etc.), etc.

In some embodiments, the processing device may determine whether the current acquisition parameters of the acquired image need to be re-determined according to the size of the overall quality score in the quality evaluation result and/or the classification result of the image. If necessary, the acquisition parameters may be determined according to the quality evaluation result. For example, according to the quality evaluation result, adjust the dose, angle, image reconstruction algorithm, position of the target subject, the position of the target subject, etc. of the ray scanning used in image acquisition to obtain a higher quality image through the determined acquisition parameters.

In some embodiments, the processing device may determine whether the acquisition parameters need to be re-determined and how to adjust the acquisition parameters according to the quality evaluation result by the method described in the following embodiments.

The processing device may determine whether the quality evaluation result meets the preset conditions; If not, the current acquisition parameters are re-determined to re-acquire the image of the target subject; If so, at least a part of the current acquisition parameters is stored as at least a part of a historical imaging protocol. The current acquisition parameters include one or more of the target subject's imaging position, image processing algorithm parameters, positioning parameters, ray source parameters, filtering kernel parameters, image denoising parameters, reconstruction parameters, artifact suppression parameters, and injection parameters.

In some embodiments, the processing device may determine whether the quality evaluation result meets the preset conditions according to whether the overall quality score in the quality evaluation result exceeds the preset score. The default score may be set to 80%, 90%, or 70% of the full score. For example, if the full score is 5, the preset score may be 4. If the preset score is reached, the quality evaluation result is considered to meet the preset conditions. In some embodiments, the processing device or doctor may also evaluate whether the quality evaluation result meets the preset requirements according to one or more of the image location classification, image disease classification, and image artifact classification included in the quality evaluation result. For example, whether the location classification (such as chest, abdomen, brain, etc.), disease classification (such as a tumor, the heart disease, the vascular disease, etc.), artifact classification (such as motion artifact, confusion artifact, chemical displacement artifact, truncation artifact, magnetic sensitivity artifact) are accurate, etc. If the classification in the quality evaluation result is accurate, it may be considered as meeting the preset conditions.

When it is determined that the quality evaluation result does not meet the preset conditions and the current acquisition parameters of the image need to be adjusted, you may further determine how to adjust the current acquisition parameters based on the score size related to the evaluation indexes. For example, in the image quality evaluation result, if the overall quality score does not reach the preset score, the score related to each evaluation index may be checked. For the evaluation index with a low score, the acquisition parameters that will affect the corresponding image quality may be modified accordingly.

In some embodiments, the processing device may use the method described in the following embodiments to re-determine the current acquisition parameters.

The current acquisition parameters are re-determined based on one or more of the acquisition parameters that adjust the imaging conditions of the target subject, at least a part of the acquisition parameters in the historical imaging protocol, and the acquisition parameters that affect the image quality corresponding to various evaluation indexes.

The imaging conditions of the target subject may include the positioning mode of the target subject, whether there is a foreign object, the location conditions of the target subject, etc. It is available to adjust the position of the target subject and the angle of the ray source. For another example, removing the odor, moving the target subject to the center of the imaging field of view, reducing the movement of the target subject or keeping it still, and so on.

At least one partial acquisition parameter in the historical imaging protocol may include one or more of the target subject's imaging position, image processing algorithm parameters, positioning parameters, ray source parameters, filter core parameters, image denoising parameters, reconstruction parameters, artifact suppression parameters, and injection parameters. In some embodiments, the processing device may take at least a part of the parameters in the historical imaging protocol that match the acquisition parameters of acquiring the current image as the current acquisition parameters. In some embodiments, the historical imaging protocol may be determined based on the posture information of the target subject (the subject to be imaged). The evaluation method of the historical imaging protocol may be seen in FIGS. 7 to 8 of the present disclosure and its related description, which will not be repeated here.

The influence on image quality corresponding to each evaluation index refers to the image anatomical structure clarity, target contrast, image signal uniformity, image noise level, and artifact suppression. The corresponding acquisition parameters refer to the parameter information that will affect the image quality. For example, image reconstruction algorithm, scanning dose, ray angle, etc.

For example, if the anatomical structure definition of the image is low, the acquisition parameters may be adjusted to improve the anatomical structure definition of the image, for example, by using a sharper filter core, enhancing the structure edge in the image domain, reducing the image denoising level, and using a larger reconstruction matrix (for example, 512*512 is increased to 1024*1024) to determine the acquisition parameters again.

If the contrast of the target portion (such as the heart, brain, etc.) is low, you may choose to create a shadow agent to enhance the contrast of the structure.

If the uniformity of the image signal is low and the image is uneven, a method such as MPR (multi-plane reconstruction) may be used for correction to improve the uniformity of the fault plane.

If the image noise level is high, the dose may be appropriately increased by adjusting the scanning dose, for example, the target subject with a larger volume; Large and width differences (such as shoulders) may increase the dosage to some angles. The image reconstruction parameters may also be adjusted, for example, adaptive filtering may be used to reduce noise, image domain denoising may be used, and the filter core used for reconstruction may be changed.

If the degree of artifact suppression is low, different methods may be used to optimize for different types of artifacts by adjusting the acquisition parameters. For example, for bar artifacts, the weights of rays at certain angles may be optimized; For annular artifacts, air correction may be performed again, or the ring removal algorithm in the image domain may be adjusted; For large cone angle artifacts, more advanced reconstruction algorithms may be used (such as iterative algorithm and depth learning method); For motion artifacts, keep the target as stable as possible during scanning.

It should be noted that the above examples are only for example purposes and are not intended to limit the scope of the present disclosure. For ordinary technicians in the art, various changes and modifications may be made under the guidance of the content of the present disclosure. For example, the above methods for adjusting acquisition parameters may be combined and modified.

In the embodiments of the present disclosure, evaluating the image quality through the evaluation model may effectively reduce the cost of manually evaluating the image quality. The evaluation model may learn a lot of image quality evaluation experience during training, which may improve the efficiency and accuracy of image quality evaluation, and the image quality evaluation may be more objective and accurate. At the same time, according to the result of the image quality evaluation, the acquisition parameters of the acquired image may be adjusted to obtain an image with better quality.

Figure 3:
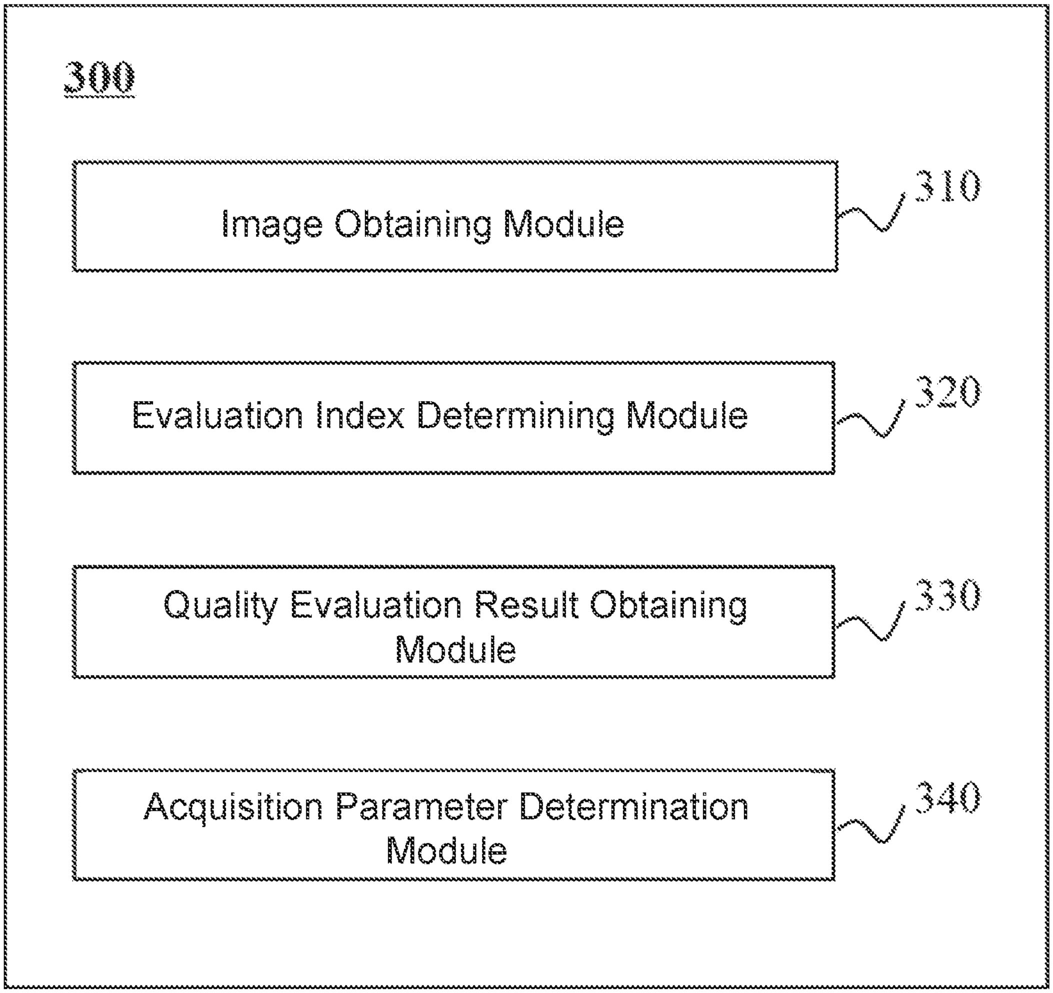
FIG. 3 is an exemplary block diagram of an image acquisition system according to some embodiments of the present disclosure.

FIG. 3 is an exemplary block diagram of an image acquisition system according to some embodiments of the present disclosure. As shown in FIG. 3, the system 300 may include an image obtaining module 310, an evaluation index determining module 320, a quality evaluation result obtaining module 330, and an acquisition parameter determination module 340.

The image obtaining module 310 may be used to acquire an image of a target subject.

The target subjects may include patients or other medical experimental objects (for example, experimental mice and other animals). The target subject may also be a part of a patient or other medical experiment object, including organs and/or tissues, such as the heart, lungs, ribs, the abdominal cavity, etc. In some embodiments, the image of the target subject may be a medical image obtained by processing the scanning projection data obtained by a detection device (such as the detector of the imaging device 110 shown in FIG. 1).

In some embodiments, the image obtaining module 310 may directly acquire the image to be evaluated from the scanning device of the scanning target subject, such as the scanning device 110, or from the storage device or the medical database. The image of the target subject may also be obtained by the image acquisition method described in FIGS. 7 and 8.

The evaluation index determining module 320 may be used to obtain the one or more scores of the image related to the one or more evaluation indexes based on one or more evaluation models.

The evaluation index is a parameter used to measure the quality of the image to be evaluated. In some embodiments, the one or more evaluation indexes may include one or more of anatomical structure clarity, target portion contrast, image signal uniformity, image noise level, artifact suppression degree, window width, window position, whether the image has foreign objects, and the position accuracy of the imaged position. The position accuracy of the imaged portion may include whether the imaged portion is located in the imaging area, whether the subject to be imaged in the image is located in a better viewing position (for example, whether it is located in the middle of the image, etc.), and so on.

The one or more scores related to the one or more evaluation indexes are obtained based on different evaluation models, respectively.

The quality evaluation result obtaining module 330 may be used to acquire the quality evaluation result of the image based on the one or more scores related to the one or more evaluation indexes.

The quality evaluation result obtaining module 330 may be used to acquire the quality evaluation result of the image based on the one or more scores related to the one or more evaluation indexes.

The acquisition parameter determination module 340 may be used to determine the acquisition parameters according to the quality evaluation result.

For more descriptions of each module of the system 400, please refer to the method section of the present disclosure, for example, the relevant descriptions of FIG. 2 and FIG. 4-FIG. 5, which will not be repeated here.

FIG. 4 a flowchart of a method for determining image quality according to some embodiments of the present disclosure. In some embodiments, the process 400 may be executed by the processing device. For example, the process 400 may be stored in a storage device (such as a built-in storage unit or an external storage device of a processing device) in the form of a program or instructions, and process 400 may be implemented when the program or instruction is executed. The process 400 may include the following operations.

Operation 402, obtaining an image to be evaluated. Operation 402 may be executed by the first obtaining module 610.

In some embodiments, the image to be evaluated may be a medical image obtained by processing the scanning projection data obtained by the detection device. For example, the imaging device 110 uses a collimated X-ray to scan the target subject. The detector receives the X-ray passing through the target subject layer. After the X-ray is converted into visible light, it is converted from an photoelectric signal to an electrical signal, and then converted by analog/digital converter to obtain scanning projection data. The image is obtained after processing the scanning projection data. Processing of projection data may be image reconstruction of scanning projection data. Image reconstruction algorithms may include analytical algorithms (such as filtered back projection algorithm), iterative algorithms (such as algebraic reconstruction algorithm, maximum likelihood algorithm), Fourier slice theorem algorithm, fan beam reconstruction algorithm, etc. The target subjects may include patients or other medical experimental objects (for example, other animals such as experimental mice), etc. The target subject may also be part of the patient or other medical experiments, including organs and/or tissues, such as the heart, lungs, ribs, abdominal cavity, etc.

In some embodiments, the detection device may include, but is not limited to, one or any combination of computer radiography (CR), digital radiography (DR), computer tomography (CT), positron emission computed tomography (PET), screen X-ray machine, mobile X-ray device (such as mobile C-arm machine), digital subtraction angiography (DSA), linear accelerator, etc. The image to be evaluated may include one or more of a computer tomography image, an X-ray projection image, phase contrast image, a dark field image, and a nuclear magnetic resonance image.

In some embodiments, the image to be evaluated may be obtained directly from the scanning device of the scanning target subject, such as the imaging device 110, or from the storage device or the medical database.

In some embodiments, the image to be evaluated may be preprocessed.

In some embodiments, the preprocessing of the image to be evaluated may be to standardize the color of each pixel in the image to be evaluated. The methods of color standardization may include graying, gamma correction, or other methods. Among them, graying may make the color of the image only have 256 values (0~255) of grayscale. Gamma correction may adjust the contrast of the image, so as to reduce the impact of local shadows and changes in image brightness, and reduce image noise. Preprocessing the image may eliminate irrelevant information in the image, restore useful real information, enhance the detectability of relevant information, and simplify data to the maximum extent, thus improving the reliability of feature extraction, image segmentation, and recognition, and improving the efficiency and accuracy of image quality evaluation.

In some embodiments, preprocessing the image to be evaluated may be to extract the image features of the image to be evaluated. The features of an image may include the gray level features of the image, the texture features of the image, the spectrum features of the image, the gradient features of the image, and the part shape (for example, the outer boundary of the object) features of the image.

In some embodiments, pre-processing evaluation images may also include the local features of the local image of the image to be evaluated. The local features of local images may include color features, texture features, shape features, and local feature points. The local features of extraction may be used to determine the image quality of the local image to further determine the quality of the image to be evaluated according to the image quality of the local image. For more descriptions of local images, please refer to FIG. 5 and related descriptions, which will not be repeated here. The features of extraction may be entered into the model (for example, evaluation models, evaluation sub-models) to determine the image quality of the image to be evaluated.

The feature extraction method may include a Histogram of Oriented Gradient (HOG), a Scale-Invariant Features Transform (SIFT), Speeded UP Robust Features, and a Local Binary Pattern (LBP), etc.

Operation 404, obtaining, based on one or more evaluation models, one or more scores related to an evaluation index of the image to be evaluated, and the evaluation index includes one or more of an anatomical structure clarity, a target portion contrast, an image signal uniformity, an image noise level, and an artifact suppression degree. The one or more scores related to the evaluation indexes may be obtained based on different evaluation models, respectively. Operation 404 may be performed by a first processing module 620.

In some embodiments, the evaluation model may be trained based on the medical images and/or natural images of biological tissues and/or organs of the target subject and their corresponding labels. The labels may be manually given scores related to different evaluation indexes. In some embodiments, the one or more scores related to the one or more evaluation indexes may be understood as the score classification of the image to be evaluated in the one or more evaluation indexes. Each category corresponds to a label, and each label corresponds to a score. For example, in five categories, the label [1, 0, 0, 0, 0] of the first category may correspond to a score of 1 point, the label [0, 1, 0, 0, 0] of the second category may correspond to a score of 2 points, the label [0, 0, 1, 0, 0] of the third category may correspond to a score of 3 points, the label [0, 0, 0, 1, 0] of the fourth category may correspond to a score of 4 points, and the label [0, 0, 0, 0, 1] of the fifth category may correspond to a score of 5 points. When classifying the evaluation indexes, since different categories of the evaluation indexes correspond to different scores, determine the category of the image to be evaluated under the evaluation index, that is, determine the score of the image to be evaluated under the evaluation index.

In some embodiments, multiple evaluation models may be obtained based on multiple training of medical images and/or natural images with known scoring labels related to different evaluation indexes, and the multiple evaluation models may be used to obtain scores under different evaluation indexes (for example, the structure clarity, the target portion contrast, the image signal uniformity, the image noise level, and the artifact suppression degree). The input of the evaluation model may be the image to be evaluated, and the output of the evaluation model may be the score related to the evaluation index of the image to be evaluated. In some embodiments, when obtaining the one or more scores related to the evaluation index, a single evaluation model may be used to obtain the one or more scores related to the single evaluation index. For example, a first evaluation model may be used to obtain the one or more scores under the anatomical structure clarity.

The evaluation index refers to a parameter used to measure the quality of the image to be evaluated. The evaluation index may include one or more of an anatomical structure clarity, a target portion contrast, an image signal uniformity, an image noise level, and an artifact suppression degree.

In some embodiments, the anatomical structure clarity may be the clarity of the texture and the boundary of each part (or each anatomical structure) of the image to be evaluated. The anatomical structure may be the anatomical structure of the portion included in the image to be evaluated. For example, if the image to be evaluated is a brain image, then the anatomical structure is a brain anatomical structure (for example, a brain, a diencephalon, a cerebellum, a brain stem, etc.). For another example, if the image to be evaluated is a kidney image, then the anatomical structure is the kidney anatomical structure (for example, a kidney cortex, a kidney medulla, etc.).

In some embodiments, the target portion contrast may be the contrast between the light area and dark area of the image to be evaluated, such as the contrast of different brightness levels between the white of the brightest area and the black of the darkest area, and may also be understood as the size of the gray scale contrast in an image. The target portion may be a portion that the patient or other medical subjects need to observe, such as the skull of the brain, the lung window of the chest, and the soft tissue of the abdomen, etc.

In some embodiments, the image signal uniformity may be the uniformity of the image signal obtained when the scanning device scans the target subject, for example, during MRI scanning, the uniformity of the size of the MRI signal generated by the hydrogen atom nucleus of the tissues and organs of the scanning target subject and/or in the lesions under the action of the external strong magnetic field.

In some embodiments, the image noise level may be the extent degree of unwanted or redundant interference information existing in the image to be evaluated. For example, some isolated noise points may exist in some areas of the image.

In some embodiments, the artifact suppression degree may be the degree of elimination or suppression degree of artifacts in the image to be evaluated.

The score related to the evaluation index may be the score of the image to be evaluated on the parameter item measuring the image quality, for example, the score of the anatomical structure clarity, the score of the target portion contrast, the score of the image signal uniformity, the score of the image noise level, and the score of the artifact suppression degree, etc. The scoring range related to each evaluation index may be set by the system 100 or the user. In some embodiments, the scoring range may be set between 1-5 points. The higher the score, the better the image quality may be. The higher the score of the anatomical structure clarity, the clearer the anatomical structure of the image to be evaluated may be, and the better the image quality may be. The higher the score of the target portion contrast, the higher the target portion contrast of the image to be evaluated may be, and the better the image quality may be. The higher the score of the image signal uniformity, the higher the image signal uniformity of the image to be evaluated may be, and the better the image quality may be. The higher the score of image noise level, indicating that the noise level of the image to be evaluated is more in line with the requirements (for example, the noise level in the uniform area of the image is lower, the area with objects contains a moderate amount of noise, or the like), the better the image quality may be. The higher the score of the artifact suppression degree, the lower the artifact level of the image to be evaluated may be, and the better the image quality may be.

In some embodiments, the scores related to the evaluation indexes may be obtained based on different evaluation models. For example, the score of anatomical structure clarity may be obtained by inputting the image to be evaluated into a first evaluation model, the score of target portion contrast may be obtained by inputting the model to be evaluated into a second evaluation model, the score of image signal uniformity may be obtained by inputting the image to be evaluated into a third evaluation model, the score of image noise level may be obtained by inputting the image to be evaluated into a fourth evaluation model, and the score of artifact suppression degree may be obtained by inputting the image to be evaluated into a fifth evaluation model. The different evaluation models refer to models with different model parameters. The type and/or structure of the evaluation models may be the same. For example, the first evaluation model, the second evaluation model, the third evaluation model, the fourth evaluation model, and the fifth evaluation model may all be classified models. The only difference is that the parameters are different. In some embodiments, the model parameters between different evaluation models may also be the same. In some embodiments, the first evaluation model, the second evaluation model, the third evaluation model, the fourth evaluation model, and the fifth evaluation model may have different model types and/or model structures.

In some embodiments, different evaluation models may be trained in the same or similar way. As an example, the evaluation model may be trained in the following ways: the input of the model is a medical image and/or a natural image with a known label, and the output of the model is a score related to the evaluation index. The output of the model may be expressed in the form of a vector representing the probability distribution of a certain label, for example, [0.05, 0.8, 0.05, 0.05, 0.05], indicating that the probability of the score related to the evaluation index of the image being 2 points is 0.8. The loss function may be constructed based on the difference between the output of the model and the label, and the value of the loss function may be less than the threshold by continuously optimizing the parameters of the model to complete the training of the model. In some embodiments, the loss function of the model may be the L1 norm of the difference between the model output and the label, the cross-entropy loss function, or the like.

In some embodiments, multiple scores related to multiple evaluation indexes may also be obtained by inputting the image to be evaluated into an evaluation model at one time. The evaluation model may be obtained by training in the same or similar way as the training method described above. For example, the input of the model is also a medical image and/or a natural image with known labels. The difference may be that known labels may be multiple labels, and the output of the model may be multiple vectors corresponding to the multiple known labels. For example, the medical image input into the model may include [0, 0, 0, 1, 0] under the anatomical structure definition index, [0, 0, 0, 0, 1] under the image signal uniformity index, [0, 0, 0, 0, 1] under the target portion contrast index, and the model output may be [0.05, 0.05, 0.05, 0.8, 0.05], [0.05, 0.05, 0.05, 0.05, 0.8], and [0.05, 0.05, 0.05, 0.05, 0.8], which respectively represents the probability of the label belonging to the anatomical structure definition index, the probability of the label belonging to the image signal uniformity index and the probability of the label belonging to the target portion contrast index. Thus, an evaluation model can be used to quickly evaluate the one or more scores related to multiple evaluation indexes of an image to be evaluated, and the efficiency of image quality evaluation can be further improved.

In some embodiments, at least one of one or more evaluation models may include a neural network model. In some embodiments, the at least one of the one or more evaluation models may include a linear regression model, a support vector machine (SVM), and the like.

Operation 406, obtaining the quality evaluation result of the image to be evaluated based on the one or more scores related to the one or more evaluation indexes. Operation 406 may be performed by a second processing module 630.

The quality evaluation result may be the overall quality score of the image to be evaluated. In some embodiments, the overall quality scoring range of the quality evaluation result may be set by the system 100 or the user. The overall quality scoring range may be consistent or inconsistent with the scoring range related to each evaluation index. For example, the overall quality score may be set between 1-5 points. The overall quality score may be used to evaluate the quality level of the image to be evaluated, which may include “unavailable”, “available”, “good” and “excellent”. For example, in 1-5 points, 1-2-points is “unavailable”, 3-points is “available”, 4-points is “good”, and 5-points is “excellent”. That is, 3-5-points means that the image to be evaluated may be used for subsequent processing, such as doctor diagnosis, brain blood flow calculation, etc.; 1-2-points means that the image to be evaluated is unavailable and needs to be rescanned or reconstructed.

In some embodiments, the weighted average operation may be performed on the scores related to the one or more evaluation indexes to obtain the overall quality score of the image to be evaluated. Different weights may be given to different evaluation indexes, and the overall quality score of the image to be evaluated may be obtained by summing up and averaging after multiplying the weights by the scores of the corresponding evaluation indexes. In some embodiments, for the images to be evaluated acquired after scanning different scanning portions, the criteria for obtaining the scores related to the evaluation indexes may be different, that is, the weight of the evaluation index may be determined according to the images of different portions of the target subject. For example, for brain images, the image quality requirements are: 1. the contrast between gray and white matter is obvious, and the boundary is clear; 2. the density of the skull base is uniform, including a Heinz dark area and vermis of the cerebellum; 3. reduce artifacts; 4. the skull should not be too thick, and the skull thickness should be close to the skull thickness of the bone algorithm; then relatively high weights may be assigned to anatomical structure clarity, target contrast portion, image signal uniformity, and artifact suppression degree, while a relatively low weight or no weight may be assigned to image noise level. For another example, for the heart portion, the image quality requirements are: 1. the coronary edge is clearly displayed; 2. vascular enhancement; 3. noise level; 4. reduce artifacts; then relatively high weights may be assigned to anatomical structure clarity, target portion contrast, image noise level, and artifact suppression degree, while a relatively low weight or no weight may be assigned to image signal uniformity. For another example, for the brain perfusion imaging, chest and abdomen imaging (vulnerable to the influence of the respiratory movement of the chest and abdomen) of the target patient, it is easy to cause artifacts in the final imaging image, so a relatively high weight may be assigned to the artifact suppression degree. It should be understood that the above examples are only for example and illustration and are not intended to be limited.

In some embodiments, the weight may be given manually based on experience, or determined in other ways. For example, the score related to the evaluation indexes and the image to be evaluated may be input into a trained weight model, and the output of the model may be the weight of each evaluation index. The weight model may be obtained by training multiple medical images with the known weight of each evaluation index. For example, the evaluation indexes of a brain medical image include an anatomical structure clarity, a target portion contrast, and an image signal uniformity, with weights of 0.4, 0.3, and 0.3 respectively. The evaluation indexes of a medical image of the heart portion include an anatomical structure clarity, a target portion contrast, an image noise level, and an artifact suppression degree, with weights of 0.3, 0.2, 0.2, and 0.3 respectively.

In some embodiments, the weighted average operation of the score related to the evaluation indexes may be performed outside the evaluation model or by the evaluation model. Outside the evaluation model, the one or more scores related to the one or more evaluation indexes may be calculated manually or by the processing device (such as the first calculation system 140) according to the weighted average formula, or in other ways, which is not limited in the present disclosure. In the evaluation model, the model used to obtain the one or more scores related to the one or more evaluation indexes and the model used to calculate the weighted average may be trained in the end-to-end joint learning mode to obtain the evaluation model. After the image to be evaluated is input into the evaluation model, the evaluation model may directly output the overall quality score of the image to be evaluated.

In some embodiments, when the overall quality score of the image to be evaluated is low (1-2) or not high (such as 3 points), image processing suggestions may also be given according to the quality evaluation result. For example, when imaging the chest and abdomen of the target patient, due to the influence of the respiratory movement of the chest and abdomen, the final image may contain a large number of artifacts, so suggestions may be given for rescanning or artifact suppression (for example, selecting an image reconstruction algorithm with a better artifact suppression effect (such as iterative reconstruction)), or the like.

In some embodiments, the quality evaluation result of the image to be evaluated may include the overall quality score of the image to be evaluated. In some embodiments, the quality evaluation result of the image to be evaluated may include one or more of a portion classification of the image to be evaluated, a disease classification of the image to be evaluated, and an artifact classification of the image to be evaluated. The portion classification of the image to be evaluated may be the result of classifying the portions of the target subject displayed in the image to be evaluated, such as a chest image, an abdomen image, or a brain image. The disease classification of the image to be evaluated may be the result of classifying the type of disease of the target subject displayed in the image to be evaluated, such as a tumor, a heart disease, a vascular disease, etc. The artifact classification of the image to be evaluated may be the result of classifying the artifact type in the image, such as a motion artifact, a confusion artifact, a chemical shift artifact, a truncation artifact, a magnetic sensitive artifact, etc.

In some embodiments, when training the evaluation model, medical images and/or natural images marked with multiple labels (such as labels for scores related to evaluation indexes, labels for overall image quality scores, portion classification labels, disease classification labels, and artifact classification labels) may be used for model training. After calculating the image, the trained evaluation model may output one or more quality evaluation results, including the overall image quality score and the portion classification of the image to be evaluated, the disease classification of the image to be evaluated, and the artifact classification of the image to be evaluated. The training method of the model may be described in other parts of the present disclosure, for example, the relevant description of operation 404.

In the technical scheme disclosed in the embodiments of the present disclosure, based on the machine learning technology, the trained model is used to evaluate the image quality and reduce the manual participation in image quality evaluation, which can effectively reduce the error rate in image quality evaluation and improve the efficiency and accuracy of image quality evaluation. In addition, it can give timely suggestions such as supplementary scanning or adjusting reconstruction methods for images with low scores, which can effectively help hospitals or doctors to control image quality and quickly filter out images that are valuable for clinical diagnosis. At the same time, the evaluation model may output the portion classification result of the image to be evaluated, the disease classification result of the image to be evaluated and the artifact classification result of the image to be evaluated, and doctors can quickly filter the image according to the classification results. For example, doctors may quickly make a clinical diagnosis according to the disease classification results, and quickly evaluate whether the image is available according to the artifact classification results, reducing the workload for image analysis.

It should be noted that the above description of process 400 is only for example and description, and does not limit the scope of application of the present disclosure. For those skilled in the art, various modifications and changes may be made to process 400 under the guidance of the present disclosure. However, these amendments and changes are still within the scope of the present disclosure. For example, changes to the process steps in the present disclosure, such as adding pre-processing steps and storage steps.

FIG. 5 is a flowchart for obtaining one or more scores related to one or more evaluation indexes according to some embodiments of the present disclosure. In some embodiments, the process 500 may be executed by the processing device. For example, the process 500 may be stored in a storage device (such as a built-in storage unit or an external storage device of a processing device) in the form of a program or instructions, which may realize the process 500 when executed. In some embodiments, the process 500 may be executed by the first processing module 620 located on the processing device. As shown in FIG. 5, the process 500 may include the following operations.

Operation 502, inputting the image to be evaluated into the feature extraction model.

In some embodiments, the evaluation model may include an evaluation sub-model and a feature extraction model. The feature extraction model may be used to determine the feature extraction position based on the image to be evaluated. The evaluation sub-model may be used to obtain the one or more scores related to the one or more evaluation indexes. In some embodiments, the image to be evaluated may also be a preprocessed image, for example, an image that has been grayed. For more description of the feature extraction position, please refer to the description of operation 504 below.

In some embodiments, the image to be evaluated may be input to the feature extraction model. In some embodiments, the image of the evaluation may also be directly input to the evaluation sub-model.

In some embodiments, the feature extraction model may be a convolutional neural network model. The evaluation sub-model may include a neural network model, a linear regression model, a support vector machine (SVM), etc.

In some embodiments, the end-to-end joint learning method may be used to jointly train the evaluation sub-model and the feature extraction model to obtain the evaluation model. For example, the evaluation model may be obtained by training medical images and/or natural images of biological tissues and/or organs and their corresponding labels. The sample data is the image with a known label, and the label is the score related to different evaluation indexes given manually. When training the evaluation model, the sample data first passes through the feature extraction model, and the feature extraction model determines the feature extraction position of the image and obtains a number of local images. The local images may be understood as the images corresponding to a number of sub-grids after a grid division of the image. For example, after the grid division of the image to be evaluated, four sub-grids, i.e., four local images, are obtained. After determining the local images, all the local images may re-enter the evaluation sub-model, and the local image may be filtered by the evaluation sub-model (for example, two local images may be filtered from four local images), and scores related to the evaluation indexes of the filtered local images may be given. After filtering the local images based on the evaluation sub-model, the unimportant parts of the local images may be filtered out, which can reduce the calculation of calculating the score related to the evaluation indexes of the image to be evaluated, and improve the efficiency of the image quality evaluation. For more descriptions of model training, please refer to FIG. 4 and its related descriptions, which will not be repeated here.

In some embodiments, one or more evaluation models may be obtained through end-to-end joint learning, such as the first evaluation model, the second evaluation model, the third evaluation model, the fourth evaluation model, the fifth evaluation model, etc.

Operation 504, determining the feature extraction position of the image to be evaluated based on the feature extraction model.

The input of the feature extraction model is the image to be evaluated, and the output is the feature extraction position of the image to be evaluated. The feature extraction position may be the positions of one or more image sub-blocks in the image to be evaluated. The feature extraction model may determine the positions of one or more sub-grids from several sub-grids after the grid division of the image to be evaluated, that is, the feature extraction position. In some embodiments, the feature extraction position is associated with the evaluation index of the image to be evaluated. For example, the feature extraction position under the anatomical structure clarity index may be the position of the anatomical structure of the target subject in the image. For another example, the feature extraction position under the artifact suppression degree index may be the position of the artifact in the image. The feature may be the feature of the image to be evaluated in the position, such as the grayscale feature of the image, the texture feature of the image, the spectrum feature of the image, the gradient feature of the image grayscale transformation, etc.

In some embodiments, the feature extraction model may determine the feature extraction position of the image to be evaluated by generating a mask vector. For example, the feature extraction model may divide the image to be evaluated into a 64*64 grid, and generate a mask vector with a length of 64*64. The element values of the mask vector correspond to the divided grid one by one.

In some embodiments, the value of the mask vector may be obtained by an activation function after the output of the convolutional neural network model. The activation function may be a Rectified Linear Unit (ReLU) function.

Operation 506, obtaining the local image corresponding to the image to be evaluated based on the feature extraction position, and extracting the local features of the local image.

In some embodiments, the local image is the part of the image corresponding to the feature extraction position in the image to be evaluated. The local image required in the image to be evaluated may be obtained according to the feature extraction position. For example, the required local image may be obtained by multiplying the corresponding elements of the mask vector based on the position correspondence relationship. In some embodiments, the image to be evaluated with a secondary feature extraction may be input to the evaluation sub-model, and the output of the evaluation sub-model may be the score related to the evaluation index of the image to be evaluated. For more description of local features, please refer to FIG. 2 and its related description.

The local images extracted from the image to be evaluated may be one or more. Convert the image used to evaluate the image quality from the entire image to be evaluated to one or more local images, and then extract the features of the local images to obtain the local features, which can simplify the features of high-dimensional image data, thus improving the efficiency of image quality evaluation, reducing the calculation amount of image quality evaluation, and improving the efficiency of image quality evaluation, in order to timely make corresponding feedback according to the image quality evaluation result (such as whether to re-scan, whether to change the image reconstruction algorithm, etc.).

In operation 508, obtaining the one or more scores related to the evaluation index based on the local features of the local image.

In some embodiments, after the local image is input to the evaluation sub-model, the evaluation sub-model may calculate according to the local features of the local image, and output the one or more scores related to the one or more evaluation indexes. For more descriptions of the evaluation indexes and the scores related to the evaluation indexes, please refer to FIG. 4 of the present disclosure and its related descriptions, which will not be repeated here.

By using the feature extraction model, representative local images at many places can be selected according to the content of the image, so that the extracted features from the local images are more representative.

The input set of the evaluation sub-model may be the features of the local image. Compared with the image features of the image to be evaluated, the local image has less data, which makes the evaluation sub-model more focused and more representative of the image quality. In this way, the efficiency of image quality evaluation can be effectively improved. At the same time, by deepening the complexity of the evaluation sub-model, better evaluation ability can be obtained while taking into account efficiency.

Using the evaluation sub-model to determine the image quality of the image can effectively reduce the cost brought by manual image quality evaluation, and at the same time, the sub-model can learn a large number of image quality evaluation experiences during training, thereby improving the efficiency and accuracy of the image quality evaluation, and image quality evaluation is more objective and accurate.

It should be noted that the above description of process 500 is only for example and description, and does not limit the scope of application of the present disclosure. For those skilled in the art, various modifications and changes may be made to the process 500 under the guidance of the present disclosure. However, these modifications and changes are still within the scope of the present disclosure.

Figure 6:
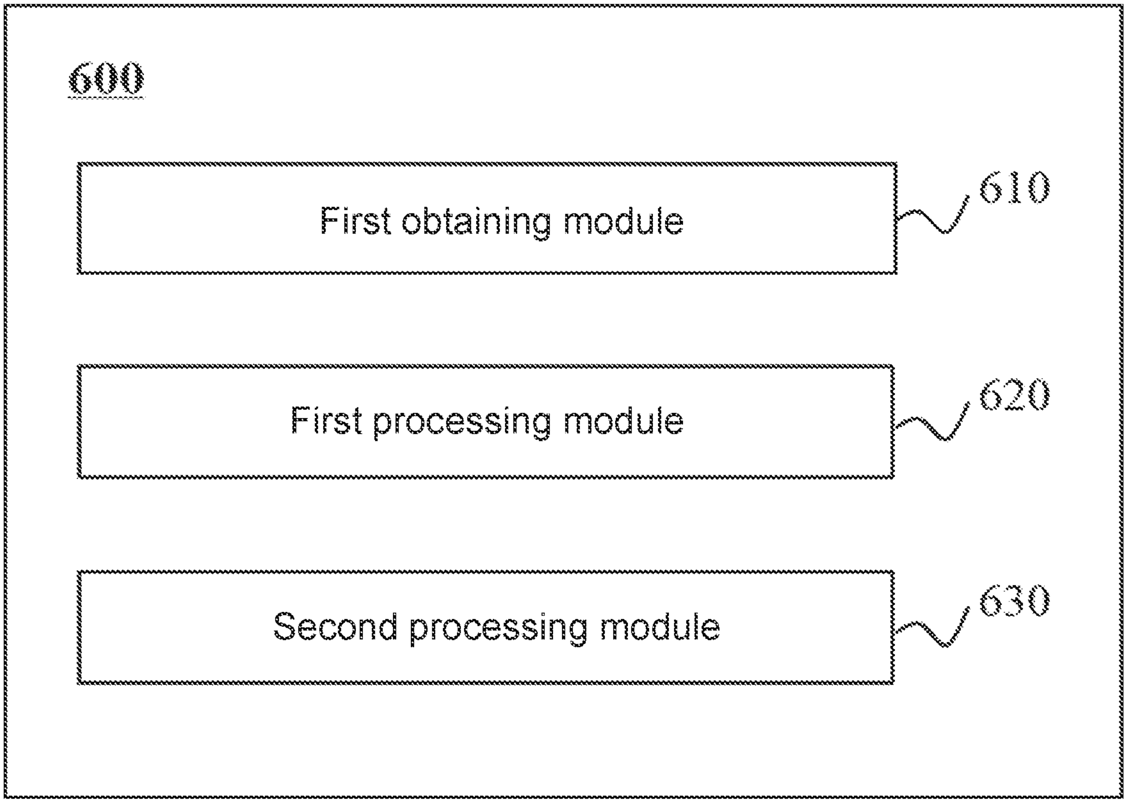
FIG. 6 is an exemplary block diagram of a system for determining image quality according to some embodiments of the present disclosure.

FIG. 6 is an exemplary block diagram of a system for determining image quality according to some embodiments of the present specification. As shown in FIG. 6, the system 600 may include a first obtaining module 610, a first processing module 620, and a second processing module 630.

The first obtaining module 610 may be configured to obtain an image to be evaluated.

The first processing module 620 may be configured to obtain the one or more scores related to the one or more evaluation indexes of the image to be evaluated based on one or more evaluation models, and the one or more evaluation indexes include one or more of an anatomical structure clarity, a target portion contrast, an image signal uniformity, an image noise level, and an artifact suppression degree. The one or more scores related to the one or more evaluation indexes may be obtained based on different evaluation models.

The second processing module 630 may be configured to obtain the quality evaluation result of the image to be evaluated based on the one or more scores related to the one or more evaluation indexes.

In some embodiments, the second processing module 630 may also be configured to perform a weighted average operation on the one or more scores related to the one or more evaluation indexes to obtain the overall quality score of the image to be evaluated.

In some embodiments, the evaluation model may include an evaluation sub-model and a feature extraction model. The feature extraction model may be used to determine the feature extraction position based on the image to be evaluated, and the feature extraction position is used to obtain the local image corresponding to the image to be evaluated. The evaluation sub-model may be used to obtain the one or more scores related to the one or more evaluation indexes based on the local features of the local image.

In some embodiments, at least one of the one or more evaluation models may include a neural network model.

In some embodiments, the image to be evaluated may include one or more of a computer tomography image, an X-ray projection image, a phase contrast image, a dark field image, and a nuclear magnetic resonance image.

In some embodiments, the quality evaluation result of the image to be evaluated may include the overall quality score of the image to be evaluated, and/or one or more of a portion classification of the image to be evaluated, a disease classification of the image to be evaluated, and an artifact classification of the image to be evaluated.

For the specific description of each module of the system for image quality evaluation, refer to the flowchart part of the present disclosure, for example, the related descriptions of FIGS. 4 to 5.

FIG. 7 is a flowchart of a method of medical image acquisition according to some embodiments of the present disclosure. Specifically, the medical image acquisition method 700 of the imaging device 110 may be executed by the processing device 140. For example, the medical image acquisition method 700 of the imaging device 110 may be stored in a storage device (such as the storage device 150) in the form of a program or instruction. When the medical image system 100 of the imaging device 110 (such as the processing device 140) executes the program or instructions, the medical image acquisition method 700 of the imaging device 110 may be implemented.

In operation 702, the posture information of the subject to be imaged may be obtained.

In operation 702, the processing device 140 may obtain the posture information of the subject to be imaged. Specifically, operation 702 may be performed by the second obtaining module 910 in the processing device 140.

In some embodiments, the subject to be imaged may include a subject for a certain part (such as head, chest), such as a patient, a physical examiner, and the like. The posture information of the subject to be imaged may be data reflecting the body shape of the subject to be imaged. In some embodiments, the posture information of the subject to be imaged may include the body size data of imaged portion, the body size data of imaged portion may be the specific size reflecting the shape of imaged portion, and the body size data of imaged portion may include at least one of the relative position of imaged portion and the frame, the thickness of imaged portion, the width of imaged portion, and height of imaged portion. The relative position between imaged portion and the frame may be the distance and angle between imaged portion and the frame (the frame of the imaging device 110). The imaged portion may be understood as the portion of the subject that needs to be scanned and imaged. The imaged portion may be the body portion corresponding to the lesion portion. For example, when a chest radiography is performed, the chest is the part to be imaged. Understandably, the imaged portion is generally the body portion that has been determined by the doctor before imaging. In some embodiments, the posture information of the subject to be imaged may include the height of the subject to be imaged.

In some embodiments, the thickness of imaged portion may be understood as the distance that the ray emitted by the ray source (for example, X-ray) passes through imaged portion. For example, when conducting a chest X-ray scanning, the X-ray needs to penetrate the chest, and the thickness of imaged portion may be the thickness of the corresponding human body shape of the chest (that is, the distance the ray passes through the human body). The thickness of the part to be imaged may affect the intensity of the ray emitted by the ray source. The width of the imaged portion may be understood as the horizontal distance from left to right of imaged portion when the subject to be imaged stands, and the height of imaged portion may be understood as the vertical distance from top to bottom of imaged portion when the subject to be imaged stands. In some embodiments, the width and height of imaged portion may affect the projection area of the ray beam. For example, the larger the area enclosed by the width and height of imaged portion (that is, the cross-sectional area of imaged portion perpendicular to the ray direction), the larger the required irradiation area may be, and the larger the projection area of the ray beam may be.

In some embodiments, the posture information of the subject to be imaged may be acquired by collecting three-dimensional (3D) contour data of the subject to be imaged. Specifically, the 3D contour data of the subject to be imaged may be acquired, and then the body size data of the imaged portion of the subject to be imaged may be obtained based on the 3D contour data of the subject to be imaged. The three-dimensional contour data may be data reflecting the body contour of the subject to be imaged. The body size data of imaged portion may include at least one of the relative position of imaged portion and the frame, the thickness of imaged portion, the width of imaged portion, and the height of imaged portion. In some embodiments, the processing device 140 may obtain the 3D contour data of the subject to be imaged through an imaging device. In some embodiments, the processing device 140 may directly obtain the 3D contour data of the subject to be imaged through a 3D imaging device. Specifically, the 3D imaging device may accurately detect the distance between each point in the image and the camera, so as to obtain the 3D spatial coordinates of each point in the image, and then model the 3D contour data (i.e., 3D model) of the subject to be imaged through the 3D spatial coordinates. In other alternative embodiments, the processing device 140 may also obtain two-dimensional (2D) image data of the subject to be imaged through several 2D imaging devices, and then perform three-dimensional reconstruction according to the two-dimensional image data to obtain the three-dimensional contour data of the subject to be imaged. In some embodiments, the processing device 140 may calculate the body size data of imaged portion based on the 3D contour data. Specifically, after obtaining the 3D contour data of the subject to be imaged, the processing device 140 may calculate the body size data of the subject to be imaged based on the 3D contour data, for example, including the height, thickness and other information of the subject to be imaged. The 3D contour data of the subject to be imaged obtained by the 3D imaging device or 2D imaging device may include the relative distance and relative angle between each point in the 3D contour data of the subject to be imaged and the 3D imaging device or 2D imaging device. Since the position (distance and angle) of the 3D imaging device or 2D imaging device relative to the frame is also determined, the relative position of imaged portion and the frame may be obtained by processing the above data. In some embodiments, if the 3D contour data includes the shape size data of the 3D contour, the processing device 140 may directly use the shape size data of the 3D contour corresponding to imaged portion as the body size data of imaged portion.

In operation 704, whether there is a matching imaging protocol in historical imaging protocols may be determined, based at least in part on the posture information of the subject to be imaged.

In operation 704, the processing device 140 may determine whether there is a matching imaging protocol in the historical imaging protocol at least based on the posture information of the subject to be imaged: if yes, designating at least a part of acquisition parameters in the matching imaging protocol as current acquisition parameters; and if no, designating default acquisition parameters as the current acquisition parameters, modifying at least a portion of the default acquisition parameters to obtain the current acquisition parameters, or inputting acquisition parameters as the current acquisition parameters. Specifically, operation 704 may be performed by the determining module 920 in the processing device 140.

Considering the validity of the stored data, the historical imaging protocol (or historical imaging protocol) corresponding to the historical imaging protocol is generally recognized by the operator, so the historical imaging protocol may be stored accordingly. In some embodiments, the historical imaging protocol may include the posture information of the historical portion to be imaged and one or more of the following information: a portion to be imaged, an algorithm parameter of image processing, a positioning parameter, and a ray source parameter. The ray source parameter may include a parameter such as a tube high voltage and/or tube current and/or current-time multiplication and/or radiation dose and/or the projection area of the radio beam. The posture information of the history imaging site may include the body size data of the historical imaging parts and the historical portion to be imaged. The posture information of the historical portion to be imaged is similar to the posture information of imaged portion. Please refer to the description of operation 702, which will not be repeated here. The positioning parameter may be the position of each device inside the imaging device 110, for example, the height and/or the irradiation angle and/or the irradiation direction reflecting the ray source relative to the imaging device. For example, the ray source is located directly above imaged portion and shines on the subject to be imaged from top to bottom, or the ray source is located in front of the side of imaged portion and shines on the subject to be imaged obliquely. The radiation dose may be the incident dose of the radiation on imaged portion, and the intensity of the incident dose may depend on the thickness of imaged portion. The projected area of the ray beam may be the ray area of the section perpendicular to the ray incidence direction, and the projected area of the ray beam may depend on the width and height of imaged portion. The algorithm parameter of image processing may be understood as the parameters used by the imaging device 110 when imaging (or reconstruction) according to the data acquired by the detector. Imaging or reconstruction may be performed according to the algorithm parameter of the image processing. The data acquired by the detector may be displayed in the form of images to facilitate the diagnosis of doctors.

A matching imaging protocol may refer to an imaging protocol with the same portion to be imaged and similar posture information (such as the height of the subject to be imaged, body size data of imaged portion, etc.). In some embodiments, the matching imaging protocol may be an imaging protocol with the same portion to be imaged and the difference with the posture information within a threshold range. Optionally, since the posture information may include at least one of the relative position of imaged portion and the frame, and the thickness of imaged portion, the width of imaged portion, and the height of imaged portion, the threshold range may include one or more of the relative angle and relative distance of imaged portion and the frame, and thickness difference, width difference, and the height difference of imaged portion. Since the posture information may also include the height of the subject to be imaged, the threshold range may include one or more of the relative angle, relative distance, height difference, thickness difference, width difference, and height difference between the subject and the frame. For example, the threshold range may include a thickness difference of 3 cm, a width difference of 2 cm, and a height difference of 2 cm. The threshold range may also be other values, which are not listed in the present disclosure. In some embodiments, the processing device 140 may, at least based on the posture information of the subject to be imaged, retrieve a historical imaging protocol to determine whether there is a matching imaging protocol. In some embodiments, the historical imaging protocol may be stored in the storage device 150, and the processing device 140 may retrieve the historical imaging protocol from the storage device 150. If there is an imaging protocol in the historical imaging protocols that is the same as imaged portion and whose difference with the posture information is within the threshold range, it may be determined that there is a matching imaging protocol in the historical imaging protocol. Otherwise, it may be determined that no matching imaging protocol in the historical imaging protocol. Specifically, after the processing device 140 acquires the posture information of the subject to be imaged (such as imaged portion and the body size data), it may search one or more stored historical imaging protocols based on search keywords (such as chest or chest x-ray), and select several historical imaging protocols as candidate imaging protocols. The candidate imaging protocols may be historical imaging protocols matching the search keywords. Further, The processing apparatus 140 may compare the posture information of the historical subject to be imaged in the candidate imaging protocol with the posture information of the current subject to be imaged, and take the candidate imaging protocol whose comparison result is within the threshold range as the current imaging protocol. In some embodiments, the search keywords may be one or more parameters included in the imaging protocol. For example, the search keywords may be the positioning information of the subject to be imaged in the imaging protocol (for example, standing imaging, side lying imaging, supine imaging, etc.), and imaged portion (for example, head, chest, etc.). In some embodiments, when the historical posture information is compared with the current posture information, it may be compared from multiple aspects. For example, the heights of the subject to be imaged may be compared, and the thickness and the widths of the imaged portion may also be compared. When the comparison result is greater than the threshold range, the processing device 140 may determine that there is no matching candidate imaging protocol. For example, the thickness of imaged portion (such as the chest) is 30 cm, while the thickness of imaged portion (such as the chest) in the candidate imaging protocol is 40 cm or 20 cm, and the difference between the two is greater than the threshold range (such as 3 cm, 5 cm, 7 cm, and so on), the processing device 140 may determine that there is no matching. When the comparison result is less than or equal to the threshold range, the processing device 140 may determine that there is a matching candidate imaging protocol. For example, the thickness of imaged portion (such as the chest) is 30 cm, while the thickness of imaged portion (such as the chest) in the candidate imaging protocol is 35 cm or 25 cm, and the difference between the two is within the threshold range (such as 5 cm, 7 cm, and so on), then the processing device 140 may determine the matching.

In some embodiments, it is also possible to determine whether there is a matching imaging protocol in the historical imaging protocol based on the name, age, gender, and imaged portion. It may be understood that the subject to be imaged has taken corresponding pictures of imaged portion in the previous period of time. During this imaging, the acquisition parameters in the previous historical imaging protocol may be directly used as the current acquisition parameters for imaging.

If it is determined that there is a matching imaging protocol in the historical imaging protocol, operation 7042 may be executed: designating at least a part of acquisition parameters in the matching imaging protocol as one or more current acquisition parameters. In some embodiments, the default acquisition parameters in the matching imaging protocol may include the acquisition parameters of the same category as those in the historical imaging protocol, such as the posture information of imaged portion and one or more of a portion to be imaged, an algorithm parameter of image processing, a positioning parameter, a radiation dose, and a projected area of a ray beam. In some embodiments, the historical imaging protocol may also include acquisition parameters different from those in the matching imaging protocol, such as the age and gender of the subject to be imaged. Therefore, at least part of the acquisition parameters in the matching imaging protocol, such as the acquisition parameters related to the imaging parameters of the imaging device 110, may be used as the current acquisition parameters.

If it is determined that no matching imaging protocol exists in the historical imaging protocol, operation 7044 may be executed: designating or at least partially modifying one or more default acquisition parameters, or inputting one or more acquisition parameters, as the one or more current acquisition parameters. In some embodiments, the default collection parameters may include the collection parameters that are the same as the category in the historical imaging protocol, for example, one or more of the posture information of the imaged portion, an image processing algorithm parameter, a positioning parameter, a radiation dose, and a projection area of a radiation beam. The default acquisition parameters may be the system's default acquisition parameters. For example, the default acquisition parameters may be factory parameters of the imaging device or some general parameters preset by experienced operators (such as technicians or doctors). When the imaging device 110 is used for imaging, the default acquisition parameters may be directly used, or the operator may modify the default acquisition parameters in part or in whole according to experience to take pictures as the current acquisition parameters. In other embodiments, if it is determined that there is no matching imaging protocol in the historical imaging protocol, no acquisition parameters may be automatically provided. At this time, the operator may input the corresponding acquisition parameters according to experience to the image.

Operation 706, an image of the subject to be imaged based on the current acquisition parameters may be captured.

In operation 706, the processing device 140 may capture an image of the subject to be imaged based on the current acquisition parameters. Specifically, operation 706 may be performed by the imaging module 930 in the processing device 140.

In some embodiments, the image may include a medical image of the subject to be imaged, such as a chest slice, a breast image, a lung image, etc.

In some embodiments, the processing device 140 may replace the acquisition parameters of the imaging device 110 with the determined current acquisition parameters, and further capture to obtain an image. Specifically, when it is determined that there is a matching imaging protocol in the historical imaging protocol, the processing device 140 may directly use the acquisition parameter of the matching imaging protocol (such as a positioning parameter and/or a ray source parameter and/or a projection area of ray beam and/or an imaging processing algorithm parameter) as the acquisition parameters of the current imaging, i.e., the acquisition parameters of the imaging device 110 are set as the acquisition parameters of the matching historical imaging protocol. Optionally, during the replacement, it may also be semi-automatic, i.e., some parameters of the protocol are from the history protocol parameters, which may be recommended to the physician. The physician may choose to use this part of the history protocol parameters and the system default parameters for other parameters. When determining that there is no matching imaging protocol in the history imaging agreement, the processing device 140 may apply the default acquisition parameter to the current imaging. The acquisition parameters in the imaging device 110 are set to the default acquisition parameters. The default acquisition parameters may be the acquisition parameters provided by the imaging device 110, or some general parameters preset by experienced operators (such as technicians or doctors).

In the embodiment of the present disclosure, the posture information of the subject to be imaged is obtained through the imaging device, and based on the posture information, the imaging protocol matching the subject to be imaged is automatically selected from the historical imaging protocol, and then the acquisition parameters in the matching imaging protocol are used to capture images, which not only improves the efficiency of image capture but also reduces the time and energy of the operator. The image quality can be used for health diagnosis by performing a quality evaluation on the image, and the image and imaging protocol passing the quality evaluation is stored to improve the diversity of data in the database.

It should be noted that the above description of the process 700 is only for example and description, and does not limit the scope of application of the present disclosure. For those skilled in the art, various amendments and changes may be made to the process 700 under the guidance of the present disclosure. However, these amendments and changes are still within the scope of the present disclosure. For example, the threshold range is not limited to the values listed in process 700, but also other values, which are not listed here.

FIG. 8 is a flowchart of a medical image quality evaluation method according to some embodiments of the present disclosure. Specifically, the medical image quality evaluation method 800 may be performed by the processing device 140. For example, the medical image quality evaluation method 800 may be stored in the storage device (such as the storage device 150) in the form of a program or instructions, and when the medical image system 100 (such as the processing device 140) performs the program or instructions, the medical image quality evaluation method 800 of the imaging device 110 may be implemented.

In operation 802, a quality of the image may be evaluated.

In operation 802, the processing device 140 may perform a quality evaluation of the image captured in operation 202. Specifically, operation 802 may be performed by the evaluation module 940 in the processing device 140.

Image quality may refer to the degree of difference between the captured image and the reference image. The smaller the difference, the higher the image quality may be. The reference image may refer to the image in which the operator may clearly observe imaged portion.

In some embodiments, the processing device 140 may evaluate the image quality. Specifically, several indexes related to the quality of the image may be determined, and whether these indexes meet a preset condition may be determined to determine whether the image quality evaluation result meet the preset condition. In some embodiments, several indexes related to the quality of the image may include an contrast, a window width, a window level, whether there is a foreign object in the image, and/or whether imaged portion of the subject to be imaged in the image is located in the imaging area.

In some embodiments, the contrast may reflect the degree of difference between light and dark areas in the image, and the processing device 140 may determine the contrast by acquiring the gray value of the image. In some embodiments, the window width of an image may refer to the display range of pixel values of the image. The pixel values of images obtained from different portions to be imaged may have the same window width, but the window levels of the pixel value may be different. In some embodiments, whether there is a foreign object in the image may be detected in the image. For example, a foreign object may include metal jewelry, a belt, etc. Because the transmission rate of the foreign object on the rays is different from the subject to be imaged, the foreign object is an object with a large difference in grayscale from tissue or bone and with a specific shape in the image. In some embodiments, whether the imaged portion is located in the imaging area may be determined by detecting whether imaged portion in the image is in a better viewing position (for example, in the middle of the image). The imaging area may be the area where the ray may reach imaged portion, for example, the corresponding position of the scanning table. When the imaged portion of the subject to be imaged is located in the middle of the imaging area, the imaged portion is located in the center of the image, which is more convenient for the operator to observe.

In some embodiments, when the contrast, the window width, and/or the window level meets a preset threshold condition, and there is no foreign object in the image and imaged portion is located in the middle of the imaging area, it may be determined that the quality evaluation result meets the preset condition. For contrast, the preset threshold condition may include the contrast range of 50:1~300:1, 100:1~400:1, or 100:1~500:1, etc. For example, when the contrast is 100:1, it is within the contrast range of 50:1~300:1, i.e., the contrast meets the preset threshold condition. For the window width, the preset threshold condition may include a window width of 50, 100, or 200. For example, when the window width is 100, the window width meets the preset threshold condition. For the window level, the preset threshold condition may include a range of pixel values with a window level of 0~100, 100~200, or 200~300. For example, when the window level is 150 and the preset threshold range is 100~200, the window level meets the preset threshold condition. The preset condition may be a preset benchmark for evaluating image quality, not a fixed condition. Specifically, when at least one of the contrast, window width or window level of the image meets the preset threshold condition, and there is no foreign object in the image and the imaged portion is located in the imaging area, the image quality is considered to meet the requirement, i.e., the quality evaluation result meets the preset condition. Conversely, for example, the contrast, window width or window position of the image meets the preset threshold condition, but when there is a foreign object in the image or imaged portion is not located in the imaging area, the image quality is considered to not meet the requirement, i.e., the quality evaluation result may not meet the preset conditions.

In operation 804, if the quality evaluation result meets a preset condition, the one or more current acquisition parameters and the posture information may be stored as at least a part of a historical imaging protocol.

In operation 804, the processing device 140 may store the current acquisition parameters and posture information as at least a part of a historical imaging protocol when the quality evaluation result meets the preset condition. Specifically, operation 320 may be performed by the recording module 950 in the processing device 140.

In some embodiments, the processing device 140 may perform the corresponding follow-up operation based on the quality evaluation result. In some embodiments, if the quality evaluation result meets the preset conditions, the processing device 140 may also store the current acquisition parameters and posture information, which may be used as at least part of a historical imaging protocol. In some embodiments, storing the current acquisition parameters and posture information as at least a part of a historical imaging protocol may be understood as that the stored historical imaging protocol may also include information other than the acquisition parameters and posture information, such as operator information, personal information of the subject to be imaged, information of imaged portion, positioning information of the subject to be imaged, etc. If the quality evaluation result meets the preset condition, it means that the image quality taken by the acquisition parameter (for example, the algorithm parameter of image processing, the positioning parameter, the radiation dose, and the projected area of the ray beam, etc.) meets the requirement, and can be used to diagnose the health of imaged portion, further indicating that the acquisition parameters used in this imaging match the posture information of the subject to be imaged (for example, body size data, etc.), and the captured image quality meets the requirement. The processing device 140 stores the relevant acquisition parameters (for example, the incident intensity of the ray) and posture information (for example, the chest thickness is 25 cm) as at least part of a historical imaging protocol, which is equivalent to binding the posture information with the acquisition parameters. When imaging subsequently, it is only necessary to determine the corresponding acquisition parameters according to the posture information of the subject to be imaged, it can avoid the inaccuracy of the default parameters of the system, and also reduce the time and energy consumed by the operator to determine the acquisition parameters, thus improving the imaging efficiency and ensuring the image quality.

In some embodiments, if the quality evaluation result meets the preset conditions, the processing device 140 may also save the currently captured image. Specifically, when the quality evaluation result meets the preset conditions, the processing device 140 may save the currently captured image as the final result of this imaging, and output it to the operator for diagnosis.

In other embodiments, if the quality evaluation result does not meet the preset condition, the operator may be prompted to remove a foreign object and/or adjust the positioning mode of imaged portion, and the current acquisition parameters are re-determined to capture the image of the subject to be imaged. Specifically, when the quality evaluation result does not meet the preset conditions (for example, the imaged portion is not located in the imaging area, an object with high brightness and specific shape appears in the image, etc.), the processing device 140 may remind the operator to adjust and re-determine the current acquisition parameters to capture the image of the subject to be imaged. For example, when an object with high brightness and a specific shape appears in the image, the operator may be notified that there is a foreign object on the subject to be imaged, and the foreign object needs to be removed and the subject needs to be imaged again. For another example, when the imaged portion is not located in the imaging area, the operator may be notified of the distance between imaged portion and the center of the imaging area. At this time, the operator may require the subject to be imaged to move to a corresponding position (for example, move to the left, move to the right, etc.) and then capture again. In some embodiments, the acquisition parameters used for re-imaging need to be re-determined, and the re-determined acquisition parameters may be the same as or different from those used for the last imaging. Specifically, since the acquisition parameters determined in operation 704 are the acquisition parameters corresponding to the historical images that have been imaged and passed the quality evaluation, and the posture information of the historical subject is consistent with the posture information of the current subject, the newly determined acquisition parameters may be the same as the acquisition parameters used in the last imaging. In some embodiments, the operator may also manually adjust the acquisition parameters. For example, when the operator finds that there are acquisition parameters that are more suitable for the posture information of the subject to be imaged according to previous experience, or finds that imaged portion is wrong during the imaging process, the operator may adjust the acquisition parameters to obtain a higher quality image. The acquisition parameters at this time are different from those used in the previous imaging.

It should be noted that the above description of process 800 is only for example and description, and does not limit the scope of application of the present disclosure. For those skilled in the art, various amendments and changes may be made to process 800 under the guidance of the present disclosure. However, these amendments and changes are still within the scope of the present disclosure. For example, the preset threshold conditions are not limited to the values listed in The process 800, but may also be other values, which are not listed here.

Figure 9:
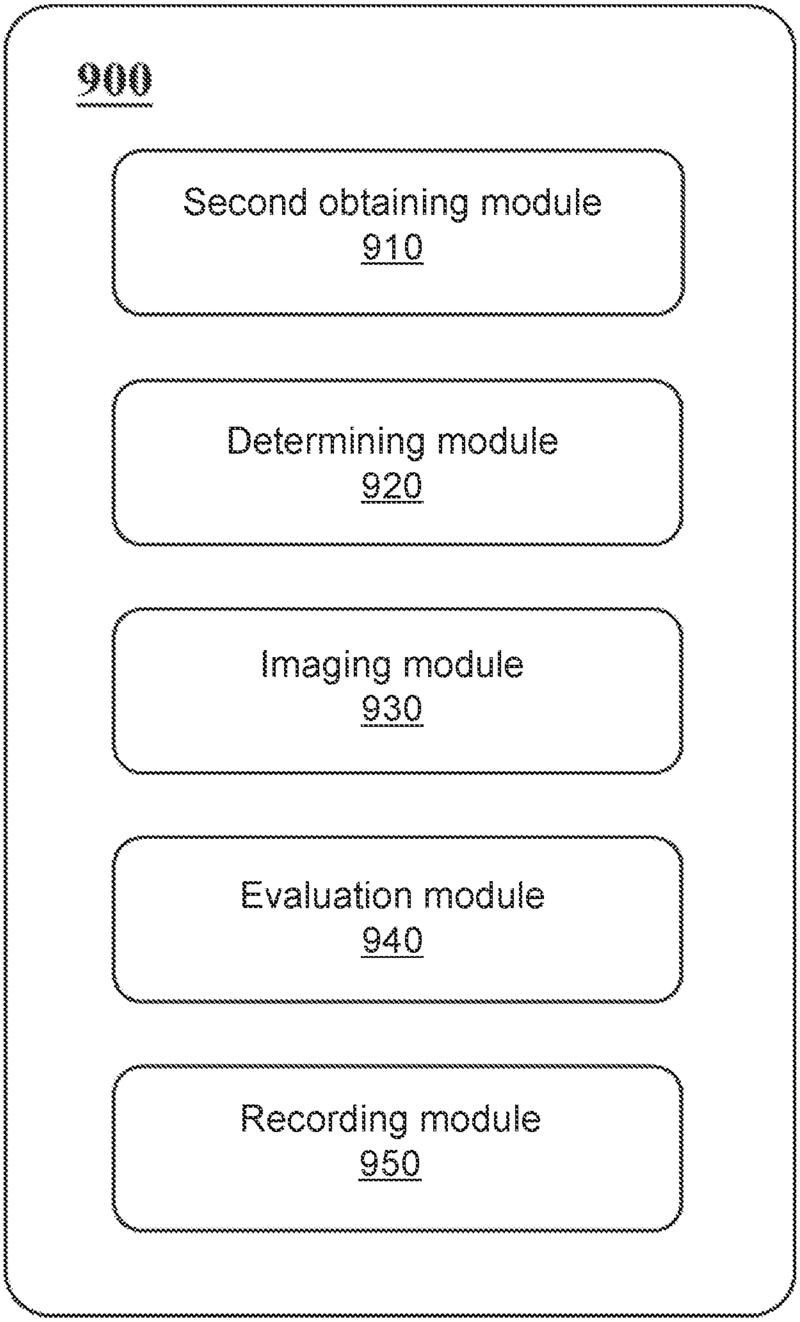
FIG. 9 is an exemplary block diagram of a medical image acquisition system according to some embodiments of the present disclosure.

FIG. 9 is an exemplary block diagram of a medical image acquisition system according to some embodiments of the present disclosure. As shown in FIG. 9, the system 900 may include a second obtaining module 910, a determining module 920, an imaging module 930, an evaluation module 940, and a recording module 950.

The second obtaining module 910 may be configured to acquire the posture information of the subject. For more information about obtaining the pose information of the subject, please refer to the description of operation 702, which will not be repeated here.

The determining module 920 may be configured to determine, based at least in part on the posture information of the subject to be imaged, whether there is a matching imaging protocol in historical imaging protocols; if yes, designating at least a part of acquisition parameters in the matching imaging protocol as current acquisition parameters; and if no, designating default acquisition parameters as the current acquisition parameters, modifying at least a portion of the default acquisition parameters to obtain the current acquisition parameters, or inputting acquisition parameters as the current acquisition parameters. For more content on whether there is a matching imaging protocol in the historical imaging protocols, please refer to the description of operation 704, which is not described here.

The imaging module 930 may be configured to capture an image of the subject to be imaged based on the current acquisition parameters. For more information about capturing an image of a subject, please refer to the description of operation 706, which will not be repeated here.

The evaluation module 940 may be configured to evaluate the image quality. In some embodiments, the evaluation module 940 may also be used to determine that the quality evaluation result meets the preset condition when the contrast, window width, and/or window level of the image meet the preset threshold condition, there is no foreign object in the image, and imaged portion is located in the imaging area. For more information on image quality evaluation, please refer to the description of operation 802.

The recording module 950 may be configured to store the current acquisition parameters and posture information as at least a part of a historical imaging protocol when the quality evaluation result meets the preset condition. For more information about storing the current collection parameters and posture information, please refer to operation 804, which will not be repeated here.

It should be understood that the system and its modules shown in the above embodiments may be implemented in various ways. For example, in some embodiments, the system and the modules may be implemented by hardware, software, or a combination of software and hardware. The hardware part may be implemented with dedicated logic. The software part may be stored in the memory and executed by an appropriate instruction execution system, such as a microprocessor or specially designed hardware. Those skilled in the art may understand that the above methods and systems may be implemented using computer executable instructions and/or included in processor control codes, for example, such codes are provided on a carrier medium such as a disk, CD or DVD-ROM, a programmable memory such as a read-only memory (firmware), or a data carrier such as an optical or electronic signal carrier. The system and its modules in the present disclosure may not only be implemented by hardware circuits such as VLSI or gate arrays, semiconductors such as logic chips and transistors, or programmable hardware devices such as field programmable gate arrays and programmable logic devices, but also by software executed by various types of processors, it may also be realized by the combination of the hardware circuit and the software (e. g., firmware).

It should be noted that the above description of each system and the modules is only for the convenience of description and does not limit the present disclosure to the scope of the embodiments. It may be understood that for those skilled in the art, after understanding the principle of the system, they may arbitrarily combine various modules or form a sub-system to connect with other modules without departing from the principle. For example, in some embodiments, the first obtaining module 610, the first processing module 620, and the second processing module 630 may be different modules in a system, or a module may realize the functions of two or more of the above modules. For example, the first obtaining module 610 and the first processing module 620 may be two modules, or one module may have both acquisition and processing functions. For example, each module may share an enclosure, and each module may also have its own enclosure. Such deformation is within the protection scope of the present disclosure.

It should be noted that different embodiments may have different beneficial effects. In different embodiments, the beneficial effects may be any one or a combination of the above, or any other beneficial effects that may be obtained.

The basic concept has been described above. Obviously, for the technicians of the arts, the above-mentioned detailed disclosure is only used as an example, and it does not constitute a limitation of the present disclosure. Although it is not explicitly stated here, those skilled in the art may make various modifications, improvements, and amendments to the present disclosure. Such modification, improvement, and amendment are recommended in the present disclosure, so such modification, improvement, and amendment still belong to the spirit and scope of the exemplary embodiments of the present disclosure.

Such modification, improvement, and amendment are recommended in the present disclosure, so such modification, improvement, and amendment still belong to the spirit and scope of the exemplary embodiments of the present disclosure. For example, “one embodiment”, “an embodiment”, and/or “some embodiments” refer to a certain feature, structure, or feature related to at least one embodiment of the present disclosure. Therefore, it should be emphasized and noted that the “one embodiment” “an embodiment” or “an alternative embodiment” mentioned twice or more in different positions in the present disclosure do not necessarily refer to the same embodiment. In addition, certain features, structures, or features in one or more embodiments of the present disclosure may be appropriately combined.

In addition, those skilled in the art may understand that various aspects of the present disclosure may be described and described through a number of patentable categories or situations, including any new and useful combination of processes, machines, products, or substances, or any new and useful improvement on them. Accordingly, various aspects of the present disclosure may be completely executed by hardware, software (including firmware, resident software, microcode, etc.), or a combination of hardware and software. The above hardware or software may be referred to as “data block”, “module”, “engine”, “unit”, “component” or “system”. Further, various aspects of the present disclosure may be represented as a computer product located in one or more computer-readable media, which includes computer-readable program coding.

The computer storage medium may comprise a propagation data signal containing a computer program code, for example, on a baseband or as part of a carrier wave. The transmitted signal may have multiple manifestations, including electromagnetic form, optical form, etc., or appropriate combination form. A computer storage medium may be any computer-readable medium other than a computer-readable storage medium, which may communicate, propagate, or transmit a program for use by connecting to an instruction execution system, device, or device. Program codes located on computer storage media may be transmitted through any suitable media, including radio, cable, optical fiber cable, RF, or similar media, or any combination of the above media.

The computer program code required for the operation of each part of the present disclosure may be written in any one or more program languages, including object-oriented programming languages such as Java, Scala, Smalltalk, Eiffel, JADE, Emerald, C++, C #, and VB NET, Python, etc., conventional programming languages such as C language, Visual Basic, Fortran 2003, Perl, COBOL 2002, PHP, ABAP, dynamic programming languages such as Python, Ruby, Groovy, or other programming languages. The program code may be run completely on the user's computer, as an independent software package on the user's computer, partly on the user's computer, partly on the remote computer, or completely on the remote computer or server. In the latter case, the remote computer may connect with the user computer through any network form, such as a local area network (LAN) or a wide area network (WAN), or connect to an external computer (such as through the Internet), or in a cloud computing environment, or use as a service, such as software as a service (SaaS).

In addition, unless explicitly stated in the claims, the sequence of processing elements and sequences, the use of numbers and letters, or the use of other names described in the present disclosure are not used to define the sequence of processes and methods in the present disclosure. Although some embodiments of the present disclosure that are currently considered useful are discussed through various examples in the above disclosure, it should be understood that such details are only for the purpose of explanation, and the additional claims are not limited to the disclosed embodiments. On the contrary, the claims are intended to cover all amendments and equivalent combinations that conform to the essence and scope of the embodiments of the description. For example, although the implementation of various components described above may be embodied in a hardware device, it may also be implemented as a software-only solution, e.g., an installation on an existing server or mobile device.

In the same way, it should be noted that, in order to simplify the expression disclosed in the present disclosure, and thus help understand one or more embodiments of the present disclosure, in the previous description of the embodiments of the present disclosure, various features are sometimes merged into one embodiment, the drawings, or the description thereof. However, the present disclosure method does not mean that the features required by the object of the present disclosure are more than those mentioned in the claims. In fact, the features of the embodiments are less than all the features of the single embodiment disclosed above.

Some embodiments use numbers that describe the number of components and attributes. It should be understood that such numbers used to describe the embodiments are modified by the modifiers "approximately", "approximately" or "generally" in some examples. Unless otherwise specified, "approximately", "approximately" or "generally" indicates that the number is allowed to vary by ±20%. Accordingly, in some embodiments, the numerical parameters used in the present disclosure and claims are approximate values, which may be changed according to the features required by individual embodiments. In some embodiments, the numerical parameter should consider the specified significant digits and adopt the method of general digit reservation. Although the numerical fields and parameters used to confirm the range breadth in some embodiments of the present disclosure are approximate values, in specific embodiments, such values are set as accurately as possible within the feasible range.

For each patent, patent application, patent application publication, and other materials referenced in the present disclosure, such as articles, books, specifications, publications, documents, etc., all of which are hereby incorporated into the present disclosure for reference. Except for the present disclosure history documents that are inconsistent with or conflict with the content of the present disclosure, the documents that limit the broadest scope of claims in the present disclosure (currently or hereafter attached to the present disclosure) are also excluded. It should be noted that if there is any inconsistency or conflict between the description, definition, and/or use of terms in the attached materials of the present disclosure and the contents of the present disclosure, the description, definition, and/or use of terms in the present disclosure shall prevail.

Finally, it should be understood that the embodiments in the present disclosure are only used to explain the principles of the embodiments in the present disclosure. Other deformations may also fall within the scope of the present disclosure. Therefore, as an example rather than a limitation, the alternative configuration of the embodiments of the present disclosure may be regarded as consistent with the teachings of the present disclosure. Accordingly, the embodiments of the present disclosure are not limited to the embodiments explicitly introduced and described in the present disclosure.

What is claimed is:

1. A method for image acquisition, implemented by a processing device, wherein the method comprises:

obtaining scanning data of a target subject by using an imaging device;

obtaining an image of the target subject by processing the scanning data or from a storage device or a medical database;

obtaining, by inputting the image of the target subject into multiple different evaluation models, multiple scores related to one or more evaluation indexes of the image, wherein each of the multiple different evaluation models is configured to output a score of one of the one or more evaluation indexes of the image, the multiple different evaluation models are trained based on different training samples;

the one or more evaluation indexes include one or more of: an anatomical structure clarity, a target portion contrast, an image signal uniformity, an image noise level, an artifact suppression degree, a window width, a window level, whether the image includes a foreign object, or a location accuracy of an imaged portion;

obtaining a quality evaluation result of the image based on the multiple scores related to the one or more evaluation indexes and displaying the quality evaluation result of the image on a terminal;

determining whether the quality evaluation result meets a preset condition;

in response to determining that the quality evaluation result does not meet the preset condition, re-determining one or more current acquisition parameters, including:

searching historical imaging protocols based on search keywords, and selecting several historical imaging protocols as candidate imaging protocols wherein the search keywords include positioning information of the target subject in an imaging protocol, the positioning information includes standing imaging, side lying imaging, or supine imaging, and the candidate imaging protocols match the search keywords;

in response to there is a candidate imaging protocol in the candidate imaging protocols that matches the imaged portion and whose posture information has a difference with posture information of the target subject that is within a threshold range, determining that there is a matching imaging protocol in the historical imaging protocols; and in response to there is no candidate imaging protocol in the candidate imaging protocols that matches the imaged portion and whose posture information has the difference with the posture information of the target subject that exceeds the threshold range, determining that there is no matching imaging protocol in the historical imaging protocols, wherein the posture information of the target subject includes one of a relative position of the imaged portion and a frame a thickness of the imaged portion, a width of the imaged portion, and a height of the imaged portion;

displaying the one or more current acquisition parameters on the terminal; and adjusting at least one of a dose, an angle, an image reconstruction algorithm, or a position of the target subject based on the one or more re-determined current acquisition parameters to re-acquire an image of the target subject.

2. The method of claim 1, wherein the one or more current acquisition parameters include one or more of: a portion of the target subject to be imaged, an image processing algorithm parameter, a positioning parameter, a ray source parameter, a filtering kernel parameter, an image denoising parameter, a reconstruction parameter, an artifact suppression parameter, or an injection parameter.

3. The method of claim 2, wherein the method further comprises:

if the quality evaluation result meets the preset condition, storing at least a part of the one or more current acquisition parameters as at least a part of a historical imaging protocol.

4. The method of claim 1, wherein re-determining the one or more current acquisition parameters includes:

re-determining the one or more current acquisition parameters based on one or more of: an adjustment regarding an imaging condition of the target subject, at least a part of acquisition parameters in historical imaging protocols, or at least one acquisition parameter that affects at least one of the multiple scores corresponding to at least one of the one or more evaluation indexes.

5. The method of claim 4, wherein the adjustment regarding the imaging condition of the target subject includes:

an adjustment regarding a positioning mode of the target subject, a removal of the foreign object, and/or an adjustment regarding the position of the target subject.

6. The method of claim 4, wherein re-determining the one or more current acquisition parameters includes re-determining the one or more current acquisition parameters based on the at least one acquisition parameter that affects the at least one of the multiple scores corresponding to the at least one of the one or more evaluation indexes, wherein re-determining the one or more current acquisition parameters based on the at least one acquisition parameter that affects at least one of the multiple scores corresponding to at least one of the one or more evaluation indexes includes:

determining one or more target evaluation indexes, wherein the at least one of the multiple scores corresponding to the one or more target evaluation indexes is below a preset threshold; and adjusting, based on the one or more target evaluation indexes, the at least one acquisition parameter that affects the one or more target evaluation indexes.

7. The method of claim 1, wherein the quality evaluation result of the image includes an overall quality score of the image, and one or more of: a classification of the imaged portion, a disease classification of the image, or an artifact classification of the image.

8. The method of claim 1, wherein one of the multiple different evaluation models includes an evaluation sub-model and a feature extraction model, wherein:

a feature extraction position is determined in the image of the target subject based on the feature extraction model, a local image corresponding to the image of the target subject is obtained based on the feature extraction position, and the evaluation sub-model obtains a score related to one of the one or more evaluation indexes based on one or more local features of the local image.

9. The method of claim 8, wherein one or more criteria for obtaining, by inputting the image of the target subject into multiple different evaluation models, the multiple scores related to the one or more evaluation indexes are different for images of the target subject acquired by scanning different scanning positions, wherein the scanning positions are body portions of the target subject corresponding to the lesion portion.

10. The method of claim 9, wherein obtaining the posture information of the target subject includes:

collecting three-dimensional contour data of the target subject, wherein the three-dimensional contour data includes a relative distance and a relative angle between each point in the three-dimensional contour data of the subject to be imaged and a three-dimensional imaging device or a two-dimensional imaging device, and the relative position between the imaged portion with respect to the gantry is obtained based on the relative distance and relative angle between each point in the three-dimensional contour data of the target subject and the three-dimensional imaging device or the two-dimensional imaging device; and obtaining body size data of the imaged portion of the target subject based on the three-dimensional contour data of the target subject.

11. The method of claim 9, wherein each of the historical imaging protocols includes posture information of a historical imaged portion and one or more types of the following information:

the imaged portion, an image processing algorithm parameter, a positioning parameter, a radiation dose, or a projection area of a radiation beam.

12. The method of claim 8, wherein the one or more local features of the local image include color features, texture features, shape features, and local feature points, and the method further includes:

determining an image quality of the local image based on the one or more local features of the local image; and determining a quality of the image of the target subject based on the image quality of the local image.

13. The method of claim 12, wherein the feature extraction model determines the feature extraction position by generating a mask vector, and the mask vector is obtained by an activation function after an output of a convolutional neural network model and the activation function is a Rectified Linear Unit (ReLU) function.

14. The method of claim 13, wherein the local image is a part of the image of the target subject corresponding to the feature extraction position in the image, and the method further includes:

obtaining the local image by multiplying corresponding elements of the mask vector based on a position correspondence relationship between the feature extraction position and the mask vector.

15. The method of claim 1, wherein the one or more evaluation indexes include the target portion contrast, the window width and/or the window level of the image, wherein the method further comprises:

when the target portion contrast, the window width and/or the window level of the image meets a preset threshold condition; when there is no foreign object in the image; and when the imaged portion is located in an imaging area, determining that the quality evaluation result meets the preset condition.

16. The method of claim 1, wherein the obtaining the quality evaluation result of the image based on the multiple scores related to the one or more evaluation indexes and displaying the quality evaluation result of the image on a terminal includes:

determining weights to the one or more evaluation indexes, wherein the weights are given by a trained weight model, an input of the trained weight model includes the multiple scores related to the one or more evaluation indexes and the image of the target subject, and an output of the trained weight model includes the weights to the one or more evaluation indexes; and obtaining an overall quality score of the image of the target subject by summing up and averaging after multiplying the weights by the multiple scores of the one or more evaluation indexes.

17. A method for medical image acquisition, implemented by a processing device, wherein the method includes:

obtaining posture information of a subject to be imaged based on three-dimensional contour data of the subject to be imaged, searching historical imaging protocols based on search keywords, and selecting several historical imaging protocols as candidate imaging protocols, wherein the search keywords include positioning information of the subject to be imaged in an imaging protocol, the positioning information includes standing imaging, side lying imaging, or supine imaging, and the candidate imaging protocols match the search keywords;

in response to there is a candidate imaging protocol in the candidate imaging protocols that matches the imaged portion and whose posture information has a difference with the posture information of the subject to be imaged that is within a threshold range, determining that there is a matching imaging protocol in the historical imaging protocols, and designating at least a part of acquisition parameters in the matching imaging protocol as one or more current acquisition parameters;

in response to there is no candidate imaging protocol in the candidate imaging protocols that matches the imaged portion and whose posture information has the difference with the posture information of the subject to be imaged that exceeds the threshold range, determining that there is no matching imaging protocol in the historical imaging protocols, and designating one or more default acquisition parameters as the one or more current acquisition parameters, modifying at least a portion of the one or more default acquisition parameters to obtain the one or more current acquisition parameters, or inputting one or more acquisition parameters as the one or more current acquisition parameters, wherein the posture information of the subject to be imaged includes one of a relative position of the imaged portion and a frame, a thickness of the imaged portion, a width of the imaged portion, and a height of the imaged portion; and adjusting at least one of a dose, an angle, an image reconstruction algorithm, or a position of the subject to be imaged based on the one or more current acquisition parameters to capture an image of the subject to be imaged based on the one or more current acquisition parameters.

* * * * *